US009403870B2

(12) United States Patent
Wu et al.

(10) Patent No.: US 9,403,870 B2
(45) Date of Patent: Aug. 2, 2016

(54) METHODS OF PHOSVITIN EXTRACTION AND PHOSPHOPEPTIDE PREPARATION FROM EGG YOLK

(75) Inventors: Jianping Wu, Edmonton (CA); Bo Lei, Edmonton (CA); Jiandong Ren, Edmonton (CA)

(73) Assignee: THE GOVERNORS OF THE UNIVERSITY OF ALBERTA, Calgary, Alberta (CA)

( * ) Notice: Subject to any disclaimer, the term of this patent is extended or adjusted under 35 U.S.C. 154(b) by 99 days.

(21) Appl. No.: 14/123,890

(22) PCT Filed: Jun. 11, 2012

(86) PCT No.: PCT/CA2012/000572
§ 371 (c)(1),
(2), (4) Date: Mar. 24, 2014

(87) PCT Pub. No.: WO2012/167370
PCT Pub. Date: Dec. 13, 2012

(65) Prior Publication Data
US 2014/0221296 A1    Aug. 7, 2014

Related U.S. Application Data

(60) Provisional application No. 61/495,505, filed on Jun. 10, 2011.

(51) Int. Cl.
| | | |
|---|---|---|
| *C07K 7/06* | (2006.01) | |
| *A23L 1/305* | (2006.01) | |
| *A23L 1/32* | (2006.01) | |
| *A61K 8/64* | (2006.01) | |
| *A61Q 19/00* | (2006.01) | |
| *A61K 8/98* | (2006.01) | |
| *C07K 14/465* | (2006.01) | |
| *C07K 7/08* | (2006.01) | |
| *A61K 38/00* | (2006.01) | |

(52) U.S. Cl.
CPC ............. *C07K 7/06* (2013.01); *A23L 1/3051* (2013.01); *A23L 1/32* (2013.01); *A61K 8/64* (2013.01); *A61K 8/981* (2013.01); *A61Q 19/00* (2013.01); *C07K 7/08* (2013.01); *C07K 14/465* (2013.01); *A61K 38/00* (2013.01); *A61K 2800/10* (2013.01)

(58) Field of Classification Search
CPC ....................................................... C07K 7/06
See application file for complete search history.

(56) References Cited

U.S. PATENT DOCUMENTS

2013/0116183 A1* 5/2013 Wu ........................... A23J 3/34
514/15.6

FOREIGN PATENT DOCUMENTS

WO    2008086431    7/2008

OTHER PUBLICATIONS

Castellani, O. et al.; Egg Yolk Phosvitin: Preparation of Metal-Free Purified Protein by Fast Protein Liquid Chromatography Using Aqueous Solvents; J. Chromatogr. B; 2003; vol. 791(1-2); pp. 273-284.
Jiang, N. et al.; Preparation of Novel Functional Oligophosphopeptides from Hen Egg Yolk Phosvitin; J. Agric. Food Chem.; 2000; vol. 48(4); pp. 990-994.
Byrne, M. et al.; Amino Acid Sequence of Phosvitin Derived from the Nucleotide Sequence of Part of the Chicken Vitellogenin Gene; Biochemistry; 1984; vol. 23(19); pp. 4275-4279.
Yutaka A. et al.; Fractionation and Characterization of Hen's Egg Yolk Phosvitin; Journal of Food Science (47); 1903-1907; 1982.
Adamson N.J. & Reynolds E.G.; Characterization of Tryptic Casein Phosphopeptides Prepared Under Industrially Relevant Conditions; Biotechnology and Bioengineering (45); 196-204; 1995.
Adamson N.J. & Reynolds E.G.; Relationship between degree of casein hydrolysis and phosphopeptide release; Journal of Dairy Research (64); 505-514; 1997.
Albright K. J. et al.; Release of Iron from Phosvitin by Heat and Food Additives; Journal of Food Science, 49; 18-81; 1984.
Zhao L. et al.; Preparation of casein phosphorylated peptides and casein non-phosphorylated peptides using alcalase; Eur. Food Res. Technol. 225; 579-584; 2007.
Anton M. et al; Thermostability of Hen Egg Yolk Granules: Contribution of Native Structure of Granules; Journal of Food Science (64), No. 4; 581-584; 2000.
Bennich H. et al; A Phosphopeptide Isolated from Bovine α-Casein after Tryptic Hydrolysis; Acta Chemica Scandinavica (13); 1171-1175; 1959.
Burley R.W. & Cook W.H.; Isolation and Composition of Avian Egg Yolk Granules and Their Constituent α- and β-Lipovitellins; Can. J. Biochem. Physiol. (39); 1295-1307; 1961.
Causeret D. et al.; Ionic Strength and pH Effects on Composition and Microstructure of Yolk Granules ; Journal of Food Science (56), No. 6; 1532-1536; 1991.
Causeret D. et al.; Mineral Cations Affect Microstructure of Egg Yolk Granules; Journal of Food Science (57), No. 5; 1323-1326; 1992.
Chang C.M. et al.; Microstructure of Egg Yolk; Journal of Food Science (47), No. 5; 1193-1200; 1977.
Chay Pak Ting B.P. et al.; Comparative Composition and Antioxidant Activity of Peptide Fractions Obtained by Ultrafiltration of Egg Yolk Protein Enzymatic Hydrolysates; Membranes 1; 149-161; 2011.
Choi I. et al.; Effectiveness of phosvitin peptides on enhancing bioavailability of calcium and its accumulation in bones; Food Chemistry (93); 577-583; 2005.
Chung S.L. & Ferrier L.K.; pH and Sodium Chloride Effects on Emulsifying Properties of Egg Yolk Phosvitin; Journal of Food Science (57), No. 1; 40-42; 1992.
Clark R.C.; The Isolation and Composition of Two Phosphoproteins from Hen's Egg; Biochem. Journal (118); 537-542; 1970.

(Continued)

*Primary Examiner* — Amber D Steele
(74) *Attorney, Agent, or Firm* — Bennett Jones LLP

(57) ABSTRACT

The invention is directed to methods for extracting phosvitin from egg yolk involving contacting the egg yolk or egg yolk protein granules with a solution having a salt concentration of about 10% to form a mixture; optionally, heating the mixture; adjusting the pH of the mixture to separate phosvitin from other proteins; recovering the phosvitin. The phosvitin extract may be dephosphorylated and hydrolyzed to produce phosvitin phosphopeptides.

24 Claims, 13 Drawing Sheets

(56) References Cited

OTHER PUBLICATIONS

Clark R.C.; The primary structure of avian phosvitins- contributions through the Edman degradation of methylmercaptovitins prepared from the constituent phosphoproteins; Int. J. Biochem. (17), No. 9; 983-988; 1985.
Cross K.J. et al.; Physicochemical Characterization of Casein Phosphopeptide-Amorphous Calcium Phosphate Nanocomplexes; The Journal of Biological Chemistry (280), No. 15; 15362-15369; 2005.
Ellegård K.H. et al.; Process scale chromatographic isolation, characterization and identification of tryptic bioactive casein phosphopeptides; International Dairy Journal 9; 639-652; 1999.
Feng F & Mine Y.; Phosvitin phosphopeptides increase iron uptake in a Caco-2 cell monolayer model; International Journal of Food Science and Technology (41); 455-458; 2006.
Finn R.N.; Vertebrate Yolk Complexes and the Functional Implications of Phosvitins and Other Subdomains in Vitellogenins; Biology of Reproduction (76); 926-935; 2007.
Goulas A. et al.; Oligophosphopeptides of Varied Structural Comptexlty Derived from the Egg Phosphoprotein, Phosvitin; Journal of Protein Chemistry (vol. 15), No. 1; 1-9; 1996.
Greengard O. et al.; Phosvitin, the iron carrier of egg yolk; Biochim. Biophys. Acta (90); 406-407; 1964.
Grogan J.; Phosphorus Nuclear Magnetic Resonance of Diverse Phosvitin Species; Comp. Biochera. PhysioL96B), No. 4; 655-663; 1990.
Hartmann R. & Meisel H.; Food-derived peptides with biological activity: from research to food applications; Current Opinion in Biotechnology, 18:163-169; 2007.
Hata I. et al.; Identification of a phosphopeptide in bovine $\alpha$-casein digest as a factor influencing proliferation and immunoglobulin production in lymphocyte cultures; Journal of Dairy Research (65); 569-578; 1998.
Hegenauer J. et al.; Staining Acidic Phosphoproteins (Phosvitin) in Electrophoretic Gels; Analytical Biochemistry; (78); 308-311; 1977.
Ishikawa S.-I. et al.; Egg Yolk Protein and Egg Yolk Phosvitin Inhibit Calcium, Magnesium, and Iron Absorptions in Rats; Journal of Food Science (72), Nr. 6; S412-S419; 2007.
Sattar Khan M.A. et al.; Molecular Mechanism of the Excellent Emulsifying Properties of Phosvitin-Galactomannan Conjugate; J. Agric. Food Chem. 47; 2262-2266; 1999.
Katayama S. et al.; Antioxidative Stress Activity of Oligophosphopeptides Derived from Hen Egg Yolk Phosvitin in Caco-2 Cells; J. Agric. Food Chem. 54; 773-778; 2006.
Katayama S. et al.; Oligophosphopeptides Derived from Egg Yolk Phosvitin Up-regulate $\gamma$-Glutamylcysteine Synthetase and Antioxidant Enzymes against Oxidative Stress in Caco-2 Cells; J. Agric. Food Chem. 55; 2829-2835; 2007.
Kawahara T. & Otani H.; Stimulatory Effects of Casein Phosphopeptide (CPP-III) on mRNA Expression of Cytokines in Caco-2 Cells; Biosci. Biotechnol. Biochem., 68 (8); 1779-1781; 2004.
Kitts D.D. & Nakamura S.; Calcium-enriched casein phosphopeptide stimulates release of IL-6 cytokine in human epithelial intestinal cell line; Journal of Dairy Research; 73; 44-48; 2006.
Kitts D.D.; Bioactive substances in food: identification and potential uses; Can. J. Physiol. Pharmacol. 42; 423-434; 1994.
Sattar Khan M.A. et al.; Effect of Protease Digestion and Dephosphorylation on High Emulsifying Properties of Hen Egg Yolk Phosvitin; J. Agric. Food Chem. 46; 4977-4981; 1998.
Korhonen H. & Pihlanto A.; Bioactive peptides: Production and functionality; International Dairy Journal, 16; 945-960; 2006.
Kurisaki J. et al.; Differences between $\alpha$- and $\beta$-Lipovitellin from Hen Egg Yolk; Agric. Biol Chem., 45 (3); 699-704; 1981.
Mc Bee L.E. & Cotterill O.J.; Ion-Echange Chromatography and Electrophoresis of Egg Yolk Proteins; Journal of Food Science, 44; 656-667; 1979.
Otani H. & Wakatsuki S.; Reduction of allergic symptoms in NC/Jic Jcl mice fed a diet containing casein phosphopeptide preparation, CPP-III; Animal Science Journal, 75; 147-153; 2004.
Peterson R.F. et al.; The Separation and Amino Acid Composition of a Pure Phosphopeptone Prepared from $\beta$- Casein by the Action of Trypsin2; vol. 80; 95-99; 1958.
Sattar Khan M.A. et al.; Bactericidal Action of Egg Yolk Phosvitin against *Escherichia coli* under Thermal Stress; J. Agric. Food Chem. 48; 1503-1506; 2000.
Schlimme E & Meisel H.; Bioactive peptides derived from milk proteins. Structural, physiological and analytical aspects; Die Nahrung 39; 1-20; 1995.
Shapiro A.L. et al.; Molecular Weight Estimation of Polypeptide Chains by Electrophoresis in SDS-Polyacrylamide Gels; Biochemical and Biophysical Research Communications; vol. 28; No. 5; 815-820; 1967.
Sundararajan T.A. et al; A simplified procedure for the preparation of phosvitin; Biochim. Biophys. Acta, 38; 360-362; 1960.
Ternes W.; Characterization of Water Soluble Egg Yolk Proteins with Isoelectric Focusing; Journal of Food Science; vol. 54, No. 3; 764-765; 1989.
Byrne B.M. et al.; Amino Acid Sequence of Phosvitin Derived from the Nucleotide Sequence of Part of the Chicken Vitellogenin Genet; Biochemistry, 23; 4275-4279 ; 1984.
Meisel H. et al.; Detection of caseinophosphopeptides in the distal ileostomy fluid of human subjects; British Journal of Nutrition; 89; 351-358; 2003.
Mecham D.K. & Olcott H.S.; Phosvitin, the Principal Phosphoprotein of Egg Yolk; vol. 71; 3670-3679; 1949.
Morris E. R. & Greene F.E.; Utilization of the Iron of Egg Yolk for Hemoglobin Formation by the Growing Rat; Journal of Nutrition; 302; 901-908; 1972.
Nakamura S. et al.; Antioxidant Activity of a Maillard-Type Phosvitin-Galactomannan Conjugate with Emulsifying Properties and Heat Stability; J. Agric. Food Chem., 46; 3958-3963; 1998.
Huopalahti R. et al.(ed.); Bioactive Egg Compounds; Springer; Berlin, Heidelberg, New York; 2007.
Tsutsui T. & Obara T.; Preparation and Characterization of Phosvitin from Hen's Egg Yolk Granule; Agric. Biol. Chem., 48 (5); 1153-1160; 1984.
Wallace R.A. & Morgan J.P.; Chromatographic resolution of chicken phosvitin. Multiple macromolecular species in a classic viteliogenin-derived phosphoprotein.; Biochem. J., 240; 871-878; 1986.
Wallace R.A. & Morgan J.P.; Isolation of Phosvitin: Retention of Small Molecular Weight Species and Staining Characteristics on Electrophoretic Gels; Analytical Biochemistry; 157; 256-261; 1986.
Xu X. et al.; Antioxidant activity of tryptic digests of hen egg yolk phosvitin; J. Sci. Food Agric., 87; 2604-2608; 2007.
Young D. et al.; Identification of Hen Egg Yolk-Derived Phosvitin Phosphopeptides and Their Effects on Gene Expression Profiling against Oxidative Stress-Induced Caco-2 Cells; J. Agric. Food Chem., 59; 9207-9218; 2011.
Young D. et al.; Egg Yolk Peptides Up-regulate Glutathione Synthesis and Antioxidant Enzyme Activities in a Porcine Model of Intestinal Oxidative Stress; J. Agric. Food Chem., 58; 7624-7633; 2010.

* cited by examiner

SEQUENCE LISTING

```
<160> NUMBER OF SEQ ID NOS: 42

<210> SEQ ID NO 1
<211> LENGTH: 34
<212> TYPE: PRT
<213> ORGANISM: Artificial Sequence
<220> FEATURE:
<223> OTHER INFORMATION: Peptide in fraction P4, PV 1-34, Domain I,
      position 1112-1145

<400> SEQUENCE: 1

Ala Glu Phe Gly Thr Glu Pro Asp Ala Lys Thr Ser Ser Ser Ser
1               5                   10                  15

Ser Ala Ser Ser Thr Ala Thr Ser Ser Ser Ser Ser Ala Ser Ser
            20                  25                  30

Pro Asn

<210> SEQ ID NO 2
<211> LENGTH: 19
<212> TYPE: PRT
<213> ORGANISM: Artificial Sequence
<220> FEATURE:
<223> OTHER INFORMATION: Peptide in fraction P4, Domain I, position
      1115-1133

<400> SEQUENCE: 2

Gly Thr Glu Pro Asp Ala Lys Thr Ser Ser Ser Ser Ser Ala Ser
1               5                   10                  15

Ser Thr Ala
```

```
<210> SEQ ID NO 3
<211> LENGTH: 10
<212> TYPE: PRT
<213> ORGANISM: Artificial Sequence
<220> FEATURE:
<223> OTHER INFORMATION: Peptide in fraction P4, Domain I, position
      1112-1120

<400> SEQUENCE: 3

Ala Glu Phe Gly Thr Pro Glu Pro Asp Ala
1               5                   10

<210> SEQ ID NO 4
<211> LENGTH: 20
<212> TYPE: PRT
<213> ORGANISM: Artificial Sequence
<220> FEATURE:
<223> OTHER INFORMATION: Peptide in fraction P4, Domain I, position
      1112-1131

<400> SEQUENCE: 4

Ala Glu Phe Gly Thr Glu Pro Asp Ala Lys Thr Ser Ser Ser Ser
1               5                   10                  15

Ser Ala Ser Ser
            20

<210> SEQ ID NO 5
<211> LENGTH: 8
<212> TYPE: PRT
<213> ORGANISM: Artificial Sequence
<220> FEATURE:
<223> OTHER INFORMATION: Peptide in fraction P4, Domain I, position
      1112-1119

<400> SEQUENCE: 5

Ala Glu Phe Gly Thr Glu Pro Asp
1               5

<210> SEQ ID NO 6
<211> LENGTH: 26
<212> TYPE: PRT
<213> ORGANISM: Artificial Sequence
<220> FEATURE:
<223> OTHER INFORMATION: Peptide in fraction P4, Domain I, position
      1120-1145

<400> SEQUENCE: 6

Ala Lys Thr Ser Ser Ser Ser Ser Ala Ser Ser Thr Ala Thr Ser
1               5                   10                  15

Ser Ser Ser Ser Ser Ala Ser Ser Pro Asn
            20                  25

<210> SEQ ID NO 7
<211> LENGTH: 31
<212> TYPE: PRT
<213> ORGANISM: Artificial Sequence
<220> FEATURE:
<223> OTHER INFORMATION: Peptide in fraction P4, Domain I, position
      1115-1145

<400> SEQUENCE: 7

Gly Thr Glu Pro Asp Ala Lys Thr Ser Ser Ser Ser Ser Ala Ser
1               5                   10                  15

Ser Thr Ala Thr Ser Ser Ser Ser Ser Ser Ala Ser Ser Pro Asn
            20                  25                  30
```

-continued

```
<210> SEQ ID NO 8
<211> LENGTH: 24
<212> TYPE: PRT
<213> ORGANISM: Artificial Sequence
<220> FEATURE:
<223> OTHER INFORMATION: Peptide in fraction P4, Domain I, position
      1122-1145

<400> SEQUENCE: 8

Thr Ser Ser Ser Ser Ser Ser Ala Ser Ser Thr Ala Thr Ser Ser Ser
1               5                   10                  15

Ser Ser Ser Ala Ser Ser Pro Asn
            20

<210> SEQ ID NO 9
<211> LENGTH: 11
<212> TYPE: PRT
<213> ORGANISM: Artificial Sequence
<220> FEATURE:
<223> OTHER INFORMATION: Peptide in fraction P4, PV 37-47, Domain II,
      position 1148-1158

<400> SEQUENCE: 9

Lys Pro Met Asp Glu Glu Glu Asn Asp Gln Val
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Peptide in fraction P4, Domain II, position
      1148-1158

<400> SEQUENCE: 10

Lys Pro Met Asp Glu Glu Glu Asn Asp Gln Val
1               5                   10

<210> SEQ ID NO 11
<211> LENGTH: 8
<212> TYPE: PRT
<213> ORGANISM: Artificial Sequence
<220> FEATURE:
<223> OTHER INFORMATION: Peptide in fraction P4, Domain II, position
      1151-1158

<400> SEQUENCE: 11

Asp Glu Glu Glu Asn Asp Gln Val
1               5

<210> SEQ ID NO 12
<211> LENGTH: 10
<212> TYPE: PRT
<213> ORGANISM: Artificial Sequence
<220> FEATURE:
<223> OTHER INFORMATION: Peptide in fraction P4, Domain II, position
      1148-1157

<400> SEQUENCE: 12

Lys Pro Met Asp Glu Glu Glu Asn Asp Gln
1               5                   10

<210> SEQ ID NO 13
<211> LENGTH: 9
<212> TYPE: PRT
<213> ORGANISM: Artificial Sequence
<220> FEATURE:
```

```
<223> OTHER INFORMATION: Peptide in fraction P4, Domain II, position
      1150-1158

<400> SEQUENCE: 13

Met Asp Glu Glu Glu Asn Asp Gln Val
1               5

<210> SEQ ID NO 14
<211> LENGTH: 22
<212> TYPE: PRT
<213> ORGANISM: Artificial Sequence
<220> FEATURE:
<223> OTHER INFORMATION: Peptide in fraction P4, PV 190-211, Domain III,
      position 1301-1322

<400> SEQUENCE: 14

Ser Gly His Leu Glu Asp Asp Ser Ser Ser Ser Ser Ser Ser Ser Val
1               5                   10                  15

Leu Ser Lys Ile Trp Gly
            20

<210> SEQ ID NO 15
<211> LENGTH: 13
<212> TYPE: PRT
<213> ORGANISM: Artificial Sequence
<220> FEATURE:
<223> OTHER INFORMATION: Peptide in fraction P4, Domain III, position
      1308-1320

<400> SEQUENCE: 15

Ser Ser Ser Ser Ser Ser Ser Ser Val Leu Ser Lys Ile
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Peptide in fraction P4, Domain III, position
      1306-1318

<400> SEQUENCE: 16

Asp Asp Ser Ser Ser Ser Ser Ser Ser Ser Val Leu Ser
1               5                   10

<210> SEQ ID NO 17
<211> LENGTH: 19
<212> TYPE: PRT
<213> ORGANISM: Artificial Sequence
<220> FEATURE:
<223> OTHER INFORMATION: Peptide in fraction P4, Domain III, position
      1301-1319

<400> SEQUENCE: 17

Ser Gly His Leu Glu Asp Asp Ser Ser Ser Ser Ser Ser Ser Ser Val
1               5                   10                  15

Leu Ser Lys

<210> SEQ ID NO 18
<211> LENGTH: 13
<212> TYPE: PRT
<213> ORGANISM: Artificial Sequence
<220> FEATURE:
<223> OTHER INFORMATION: Peptide in fraction P4, Domain III, position
      1307-1319

<400> SEQUENCE: 18
```

Asp Ser Ser Ser Ser Ser Ser Ser Val Leu Ser Lys
1               5                   10

<210> SEQ ID NO 19
<211> LENGTH: 14
<212> TYPE: PRT
<213> ORGANISM: Artificial Sequence
<220> FEATURE:
<223> OTHER INFORMATION: Peptide in fraction P4, Domain III, position
      1304-1317

<400> SEQUENCE: 19

Leu Glu Asp Asp Ser Ser Ser Ser Ser Ser Ser Val Leu
1               5                   10

<210> SEQ ID NO 20
<211> LENGTH: 14
<212> TYPE: PRT
<213> ORGANISM: Artificial Sequence
<220> FEATURE:
<223> OTHER INFORMATION: Peptide in fraction P4, Domain III, position
      1306-1319

<400> SEQUENCE: 20

Asp Asp Ser Ser Ser Ser Ser Ser Ser Val Leu Ser Lys
1               5                   10

<210> SEQ ID NO 21
<211> LENGTH: 14
<212> TYPE: PRT
<213> ORGANISM: Artificial Sequence
<220> FEATURE:
<223> OTHER INFORMATION: Peptide in fraction P4, Domain III, position
      1307-1320

<400> SEQUENCE: 21

Asp Ser Ser Ser Ser Ser Ser Ser Val Leu Ser Lys Ile
1               5                   10

<210> SEQ ID NO 22
<211> LENGTH: 9
<212> TYPE: PRT
<213> ORGANISM: Artificial Sequence
<220> FEATURE:
<223> OTHER INFORMATION: Peptide in fraction P4, Domain III, position
      1312-1320

<400> SEQUENCE: 22

Ser Ser Ser Ser Val Leu Ser Lys Ile
1               5

<210> SEQ ID NO 23
<211> LENGTH: 11
<212> TYPE: PRT
<213> ORGANISM: Artificial Sequence
<220> FEATURE:
<223> OTHER INFORMATION: Peptide in fraction P4, Domain III, position
      1310-1320

<400> SEQUENCE: 23

Ser Ser Ser Ser Ser Ser Val Leu Ser Lys Ile
1               5                   10

<210> SEQ ID NO 24
<211> LENGTH: 18
<212> TYPE: PRT
<213> ORGANISM: Artificial Sequence

```
<220> FEATURE:
<223> OTHER INFORMATION: Peptide in fraction P4, Domain III, position
      1301-1318

<400> SEQUENCE: 24

Ser Gly His Leu Glu Asp Asp Ser Ser Ser Ser Ser Ser Ser Ser Val
1               5                   10                  15

Leu Ser

<210> SEQ ID NO 25
<211> LENGTH: 18
<212> TYPE: PRT
<213> ORGANISM: Artificial Sequence
<220> FEATURE:
<223> OTHER INFORMATION: Peptide in fraction P4, Domain III, position
      1305-1322

<400> SEQUENCE: 25

Glu Asp Asp Ser Ser Ser Ser Ser Ser Ser Val Leu Ser Lys Ile
1               5                   10                  15

Trp Gly

<210> SEQ ID NO 26
<211> LENGTH: 19
<212> TYPE: PRT
<213> ORGANISM: Artificial Sequence
<220> FEATURE:
<223> OTHER INFORMATION: Peptide in fraction P4, Domain III, position
      1304-1322

<400> SEQUENCE: 26

Leu Glu Asp Asp Ser Ser Ser Ser Ser Ser Ser Val Leu Ser Lys
1               5                   10                  15

Ile Trp Gly

<210> SEQ ID NO 27
<211> LENGTH: 20
<212> TYPE: PRT
<213> ORGANISM: Artificial Sequence
<220> FEATURE:
<223> OTHER INFORMATION: Peptide in fraction P4, Domain III, position
      1301-1320

<400> SEQUENCE: 27

Ser Gly His Leu Glu Asp Asp Ser Ser Ser Ser Ser Ser Ser Ser Val
1               5                   10                  15

Leu Ser Lys Ile
            20

<210> SEQ ID NO 28
<211> LENGTH: 15
<212> TYPE: PRT
<213> ORGANISM: Artificial Sequence
<220> FEATURE:
<223> OTHER INFORMATION: Peptide in fraction P4, Domain III, position
      1306-1320

<400> SEQUENCE: 28

Asp Asp Ser Ser Ser Ser Ser Ser Ser Val Leu Ser Lys Ile
1               5                   10                  15

<210> SEQ ID NO 29
<211> LENGTH: 15
<212> TYPE: PRT
<213> ORGANISM: Artificial Sequence
```

```
<220> FEATURE:
<223> OTHER INFORMATION: Peptide in fraction P4, Domain III, position
      1304-1318

<400> SEQUENCE: 29

Leu Glu Asp Asp Ser Ser Ser Ser Ser Ser Ser Val Leu Ser
1               5                   10                  15

<210> SEQ ID NO 30
<211> LENGTH: 16
<212> TYPE: PRT
<213> ORGANISM: Artificial Sequence
<220> FEATURE:
<223> OTHER INFORMATION: Peptide in fraction P4, Domain III, position
      1304-1319

<400> SEQUENCE: 30

Leu Glu Asp Asp Ser Ser Ser Ser Ser Ser Ser Val Leu Ser Lys
1               5                   10                  15

<210> SEQ ID NO 31
<211> LENGTH: 16
<212> TYPE: PRT
<213> ORGANISM: Artificial Sequence
<220> FEATURE:
<223> OTHER INFORMATION: Peptide in fraction P4, Domain III, position
      1307-1322

<400> SEQUENCE: 31

Asp Ser Ser Ser Ser Ser Ser Ser Val Leu Ser Lys Ile Trp Gly
1               5                   10                  15

<210> SEQ ID NO 32
<211> LENGTH: 17
<212> TYPE: PRT
<213> ORGANISM: Artificial Sequence
<220> FEATURE:
<223> OTHER INFORMATION: Peptide in fraction P4, Domain III, position
      1301-1317

<400> SEQUENCE: 32

Ser Gly His Leu Glu Asp Asp Ser Ser Ser Ser Ser Ser Ser Val
1               5                   10                  15

Leu

<210> SEQ ID NO 33
<211> LENGTH: 17
<212> TYPE: PRT
<213> ORGANISM: Artificial Sequence
<220> FEATURE:
<223> OTHER INFORMATION: Peptide in fraction P4, Domain III, position
      1304-1320

<400> SEQUENCE: 33

Leu Glu Asp Asp Ser Ser Ser Ser Ser Ser Ser Val Leu Ser Lys
1               5                   10                  15

Ile

<210> SEQ ID NO 34
<211> LENGTH: 12
<212> TYPE: PRT
<213> ORGANISM: Artificial Sequence
<220> FEATURE:
<223> OTHER INFORMATION: Peptide in fraction P4, Domain III, position
      1306-1317

<400> SEQUENCE: 34
```

```
Asp Asp Ser Ser Ser Ser Ser Ser Ser Val Leu
1               5                   10
```

<210> SEQ ID NO 35
<211> LENGTH: 17
<212> TYPE: PRT
<213> ORGANISM: Artificial Sequence
<220> FEATURE:
<223> OTHER INFORMATION: Peptide in fraction P4, Domain III, position
      1306-1322

<400> SEQUENCE: 35

```
Asp Asp Ser Ser Ser Ser Ser Ser Ser Val Leu Ser Lys Ile Trp
1               5                   10                  15

Gly
```

<210> SEQ ID NO 36
<211> LENGTH: 21
<212> TYPE: PRT
<213> ORGANISM: Artificial Sequence
<220> FEATURE:
<223> OTHER INFORMATION: Peptide in fraction P4, Lipovitellin, Domain
      IV, position 1056-1076

<400> SEQUENCE: 36

```
Ile Ile Thr Glu Val Asn Pro Glu Ser Glu Glu Glu Asp Glu Ser Ser
1               5                   10                  15

Pro Tyr Glu Asp Ile
            20
```

<210> SEQ ID NO 37
<211> LENGTH: 17
<212> TYPE: PRT
<213> ORGANISM: Artificial Sequence
<220> FEATURE:
<223> OTHER INFORMATION: Peptide in fraction P4, Domain IV, 1056-1072

<400> SEQUENCE: 37

```
Ile Ile Thr Glu Val Asn Pro Glu Ser Glu Glu Glu Asp Glu Ser Ser
1               5                   10                  15

Pro
```

<210> SEQ ID NO 38
<211> LENGTH: 17
<212> TYPE: PRT
<213> ORGANISM: Artificial Sequence
<220> FEATURE:
<223> OTHER INFORMATION: Peptide in fraction P4, Domain IV, position
      1060-1076

<400> SEQUENCE: 38

```
Val Asn Pro Glu Ser Glu Glu Glu Asp Glu Ser Ser Pro Tyr Glu Asp
1               5                   10                  15

Ile
```

<210> SEQ ID NO 39
<211> LENGTH: 18
<212> TYPE: PRT
<213> ORGANISM: Artificial Sequence
<220> FEATURE:
<223> OTHER INFORMATION: Peptide in fraction P4, Domain IV, position
      1059-1076

<400> SEQUENCE: 39

```
Glu Val Asn Pro Glu Ser Glu Glu Glu Asp Glu Ser Ser Pro Tyr Glu
1               5                   10                  15

Asp Ile

<210> SEQ ID NO 40
<211> LENGTH: 9
<212> TYPE: PRT
<213> ORGANISM: Artificial Sequence
<220> FEATURE:
<223> OTHER INFORMATION: Peptide in fraction P4, Domain IV, position
      1068-1076

<400> SEQUENCE: 40

Asp Glu Ser Ser Pro Tyr Glu Asp Ile
1               5

<210> SEQ ID NO 41
<211> LENGTH: 14
<212> TYPE: PRT
<213> ORGANISM: Artificial Sequence
<220> FEATURE:
<223> OTHER INFORMATION: Peptide in fraction P4, Domain IV, position
      1059-1072

<400> SEQUENCE: 41

Glu Val Asn Pro Glu Ser Glu Glu Glu Asp Glu Ser Ser Pro
1               5                   10

<210> SEQ ID NO 42
<211> LENGTH: 14
<212> TYPE: PRT
<213> ORGANISM: Artificial Sequence
<220> FEATURE:
<223> OTHER INFORMATION: Peptide in fraction P4, Domain IV, position
      1060-1073

<400> SEQUENCE: 42

Val Asn Pro Glu Ser Glu Glu Glu Asp Glu Ser Ser Pro Tyr
1               5                   10
```

METHODS OF PHOSVITIN EXTRACTION AND PHOSPHOPEPTIDE PREPARATION FROM EGG YOLK

FIELD OF THE INVENTION

The invention relates to methods for extracting phosvitin from egg yolk, and preparing phosvitin phosphopeptides.

BACKGROUND OF THE INVENTION

Eggs have long been recognized as a source of high-quality protein and other important nutrients in the human diet. Phosvitin is a principal phosphoprotein present in egg yolk and represents about 11% of egg yolk proteins and 4% of yolk dry matter. Phosvitin is derived from the large multidomain vitellogenin precursors, which are synthesized in the liver of vertebrates under stimulation of estrogen and later cleaved into phosvitin, lipovitellin and other proteins (Finn, 2007). Phosvitin contains 12% of nitrogen and 10% of phosphorus, and has a molecular weight of 35 kDa (Mecham and Olcott, 1949; Powrie and Nakai, 1986). Phosvitin contains 217 amino acid residues, of which 123 are serine (Byrne et al., 1984). Of the 123 serine residues, 118 are phosphorylated, making it the most highly phosphorylated protein in nature (Byrne et al., 1984; Clark, 1985; Grogan et al., 1990). Due to the large amount of negatively charged phosphoserine residues, phosvitin exhibits strong metal chelating ability, and is believed to provide metal ions during embryonic development (Taborsky, 1983). Phosvitin exhibits numerous other biological properties including antioxidant and anti-bacterial abilities, and excellent emulsion-stabilizing properties (Albright et al., 1984; Chung and Ferrier, 1992; Nakamura et al., 1998; Sattar Khan et al., 2000).

Phosvitin may exhibit greater metal-chelating ability than casein phosphopeptides which are the phosphorylated fragments derived from bovine milk casein digests and are currently used as calcium supplementing agents. A subunit of casein phosphate has only one to thirteen phosphoserine residues to stabilize amorphous calcium phosphate, whereas a molecule of phosvitin has a greater number of phosphoserine residues, implying higher calcium chelating capacity. Phosvitin may thus serve as a source for the production of bioactive peptides that may improve calcium availability in vivo and increase incorporation of calcium into bone (Choi et al., 2005). Since calcium and phosphorus can be simultaneously supplied, phosvitin peptides may be useful in preventing osteoporosis in women and bone loss in aging population.

However, phosvitin is usually considered nutritionally negative due to its strong affinity to metal ions and resistance to proteolytic actions of proteases (Goulas et al., 1996). 95% of the iron in egg yolk is bound to this protein, but only 30% is biologically available (Greegard et al., 1964; Morris and Greene, 1972). Egg yolk protein and phosvitin may inhibit calcium, magnesium and iron absorptions (Ishikawa, 2007). In contrast, casein phosphopeptides enhance vitamin D independent bone calcification in rachitic children (Mellander and Isaksson, 1950; Mellander, 1950). Phosphoserine residues in casein phosphopeptides play a key role by forming soluble organophosphate salts with calcium to limit its precipitation in the distal ileum (Meisel et al., 2003). The common motif, which consists of three phosphoserine residues and two glutamic acids (Ser(P)-Ser(P)-Ser(P)-Glu-Glu) is widely recognized to contribute to the metal chelating ability of casein phosphopeptides (West and Towers, 1976; Schlimme and Meisel, 1995).

Unlike casein phosphopeptides, common knowledge about phosvitin-derived phosphopeptides is limited due to insufficient hydrolysis. The strong negatively charged side chain of phosvitin hinders the enzymatic access to cleavage sites, so the core of phosvitin remains intact after hydrolysis (Goulas et al., 1996; Khan et al., 1998). Compared with casein, which contains no more than fifteen phosphoserine residues in total and three consecutive phosphoserines in a run (Swaisgood, 2003), phosvitin could be an ideal protein source to produce phosphopeptides, since it contains as many as 123 phosphoserine residues and many of them are in consecutive runs (Grogan et al., 1990).

Phosvitin phosphopeptides exhibit antioxidant activities and calcium-absorption promoting ability in vitro and in situ (Jiang and Mine, 2000; Feng and Mine, 2006; Katayama et al., 2006; Katayama et al., 2007; Xu et al., 2007; Young et al., 2011). However, their application has been hindered by the lack of efficient and economic methods to extract phosvitin from egg yolk and to prepare phosphopeptides.

Phosvitin has been precipitated from egg yolk using magnesium sulfate, followed by ammonium sulfate and ethyl ether extraction (Mecham and Olcot, 1949). The purity of phosvitin (expressed as atomic ratio of nitrogen to phosphorus or "N/P") was 2.72 with an estimate recovery of 60-70% from egg yolk. Another method involves using butanol to remove lipovitellin, recovering phosvitin by repeated precipitation at pH 1.8, purifying with ether and ammonia extraction, and finally precipitating phosvitin using magnesium sulfate (Sundararajan et al., 1960). The resultant N/P ratio was 2.65. A simplified approach involved diluting egg yolk ten-fold with water to prepare an egg yolk pellet, extracting the lipids in the pellet using hexane/ethanol (v/v, 3/1), and extracting phosvitin with 1.74 M sodium chloride, followed by lyophilization (Losso and Nakai, 1994). The purity of the phosvitin, expressed as N/P ratio, was 3.60. A larger N/P ratio may be related to protein impurities and lower purity. Extraction was improved by conducting 10% sodium chloride extraction and magnesium sulfate precipitation, resulting in a N/P ratio of 3.5 and a yield of 3.3 g per 100 g of dried egg yolk (Castellani et al., 2003). However, such methods are of small scale, inefficient, mediocre in purity, and rely upon organic solvents and non-food compatible chemicals such as magnesium sulfate.

Therefore, there is a need in the art for improved methods of extracting phosvitin, and preparing phosvitin phosphopeptides.

SUMMARY OF THE INVENTION

The present invention relates to methods for extracting phosvitin from egg yolk, and preparing phosvitin phosphopeptides.

In one aspect, the invention comprises a process for extracting phosvitin from egg yolk comprising the steps of:

a) contacting the egg yolk or egg yolk protein granules with a salt solution to form a mixture;

b) adjusting the pH of the mixture to precipitate non-phosvitin proteins and leave phosvitin substantially in solution; and c) recovering a fraction comprising phosvitin.

In one embodiment, egg yolk is diluted and mixed with water to produce egg yolk protein granules. The mixture of egg yolk or egg yolk proteins and salt solution may be heated, prior to the pH adjustment step. The adjusted pH may be about pH 7.0 or lower.

In another aspect, the invention may comprise a method of preparing phosvitin phosphopeptides, comprising the steps of dephosphorylating phosvitin, egg yolk, or an egg yolk fraction comprising phosvitin and hydrolyzing the dephosphorylated phosvitin. In one embodiment, the phosvitin may be dephosphorylated with an alkaline solution, such as a solution of sodium hydroxide (NaOH).

In one embodiment, the extracted phosvitin, or egg yolk, or an egg yolk fraction comprising phosvitin, is hydrolyzed with proteases such as trypsin, pancreatin, pepsin, thermolysin (from *Bacillus thermoproteolyticus rokko*), α-chymotrypsin (bovine pancreas), Protex 6L (from *Bacillus licheniformis*), protex 30L (derived from *Bacillus subtilis*), or protex 7L (from *Bacillus amyloliquefaciens*). The hydrolysis may be conducted using pancreatin at an enzyme/substrate ratio of about 1:50 (w/w). The resulting phosvitin hydrolysate may have a degree of hydrolysis of greater than about 6%, or greater than about 10%. In one embodiment, the degree of hydrolysis is about 12.9%. In one embodiment, the hydrolysate has a nitrogen to phosphorus (N/P) of less than about 5, or less than about 4. In one embodiment, the phosvitin hydrolysate comprises at least one phosvitin phosphopeptide.

In another aspect, the invention comprises high purity phosvitin obtained by a process as claimed or described herein. In one embodiment, the phosvitin may have a purity in a range of about 50% to about 95%.

In another aspect, the invention may comprise a phosvitin hydrolysate, which comprises phosvitin phosphopeptides. The hydrolysate may be produced from high-purity phosvitin, a phosvitin extract having a widely varying purity, from egg yolk itself, or an egg yolk fraction comprising phosvitin.

In yet another aspect, the invention may comprise a pharmaceutical or nutraceutical composition comprising a high-purity phosvitin, or the above phosphopeptide, in combination with one or more pharmaceutically acceptable carriers, or a foodstuff comprising a high-purity phosvitin, or the above phosphopeptide.

In yet another aspect, the invention may comprise a method of promoting health by administering to a subject the pharmaceutical or nutraceutical composition or a foodstuff described above, in an amount sufficient to effect a health benefit.

Additional aspects and advantages of the present invention will be apparent in view of the description, which follows. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The invention will now be described by way of an exemplary embodiment with reference to the accompanying simplified, diagrammatic, not-to-scale drawings:

FIG. 12A shows the total ion chromatogram of P-4 fraction. FIG. 12B shows a mass spectrum of a selected time at 22.62 min. FIG. 12C shows the MS/MS spectrum of the ion m/z 1167.7. Losses of $H_3PO_4$ (98 Da) were detected as can be seen in the MS/MS spectrum. Ions with a (*) represent phosphorylated form of the ions. Ions with a)(°) represent dephosphorylated form of the ions.

DETAILED DESCRIPTION OF PREFERRED EMBODIMENTS

The present invention relates to methods for extracting phosvitin from egg yolk, and preparing phosvitin phosphopeptides.

When describing the present invention, all terms not defined herein have their common art-recognized meanings. To the extent that the following description is of a specific embodiment or a particular use of the invention, it is intended to be illustrative only, and not limiting of the claimed invention. The following description is intended to cover all alternatives, modifications and equivalents that are included in the spirit and scope of the invention, as defined in the appended claims.

"Phosvitin" is a principal phosphoprotein present in egg yolk with a molecular mass of about 35 kD and contains about 10% phosphorus. A "phosvitin extract" is a fraction extracted from egg yolk and which comprises phosvitin.

A "peptide" is a short polymer of amino acids linked by peptide bonds. A "phosphopeptide" is a peptide which incorporates at least one phosphate group. A "phosvitin phosphopeptide" is derived from phosvitin and may include phosphopeptides derived from proteins which remains associated with phosvitin during the extraction process described herein, such as lipovitellin.

In one embodiment, the present invention is directed to methods for extracting phosvitin from egg yolk, and preparing phosvitin phosphopeptides. Since the intention is to create value-added phosvitin and phosvitin-derived phosphopeptides, and pharmaceutical compositions and foodstuffs comprising same for human and/or animal consumption, the use of organic solvents and/or non-food compatible chemicals is preferably avoided. The process of the present invention is thus preferably carried out without any organic solvent and/or non-food compatible chemicals. As will be appreciated by those skilled in the art, a process which does not require the use of any organic solvent or toxic chemicals positively impacts the environment and dairy, food, pharmaceutical, and cosmetic industries. Further, the method of the present invention provides purity and recovery rates which may be beneficial in a large scale.

In one embodiment, the process for extracting phosvitin from egg yolk comprises the steps of:

a) contacting the egg yolk or egg yolk protein granules with a solution having a salt concentration of about 10% to form a mixture;

b) optionally, heating the mixture;

c) adjusting the pH of the mixture to precipitate non-phosvitin components; and d) recovering a fraction comprising phosvitin.

Figure 1:
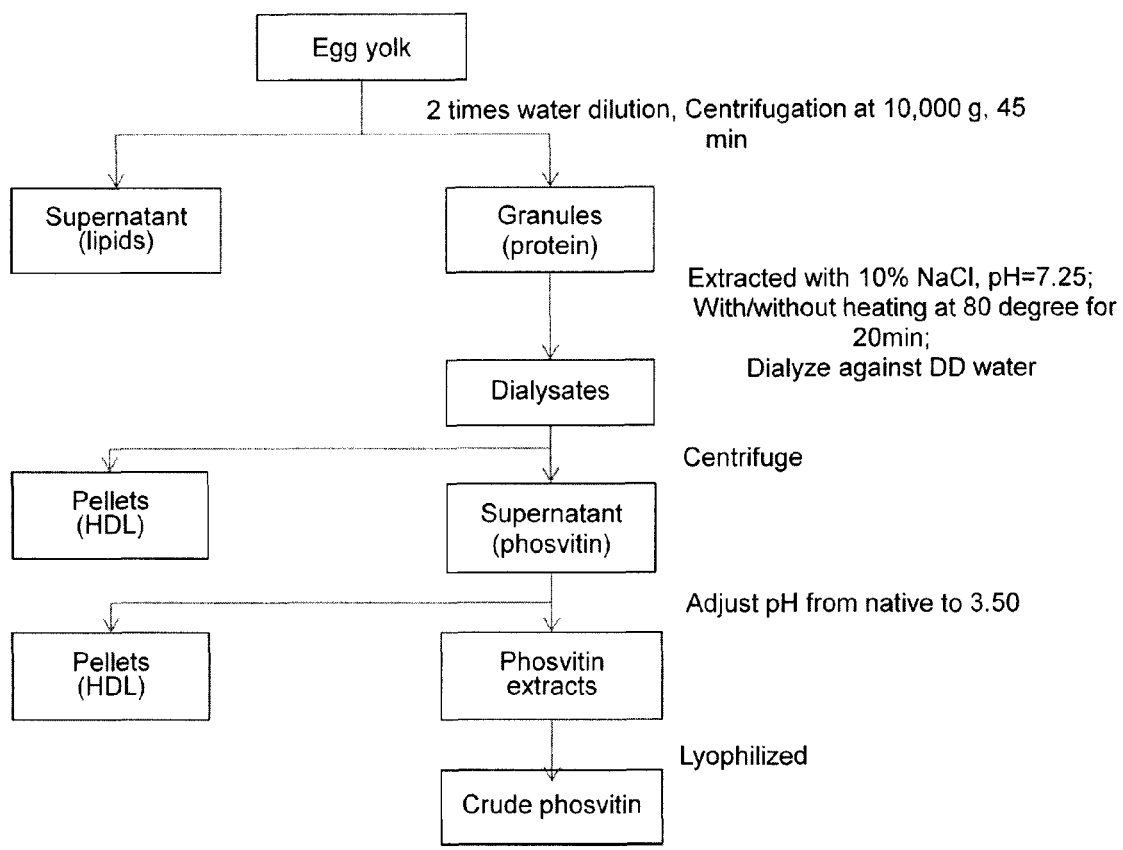
FIG. 1 is a schematic diagram showing one embodiment of the method of the present invention.

As generally shown in FIG. 1, the steps of the process to extract phosvitin are generally as follows. Fresh egg yolk, such as chicken egg yolk, is used as the starting material (Example 2). Egg yolk components include protein granules, lipids, and phospholipids. The egg yolk may be used directly, or may initially be diluted with deionized water in a ratio of ranging from 1:1 to 1:20, preferably about 1:2 (v/v), and then centrifuged to yield a precipitate comprising protein granules and a supernatant comprising lipids. The precipitate comprising protein granules is collected and used for phosvitin preparation.

The protein granules comprise phosvitin in the form of a high density lipoprotein (HDL)-phosvitin complex in protein granules. Since phosvitin is a salt-soluble protein, the protein granules are extracted using a solution having a high salt concentration to solubilize the HDLs and phosvitin, and to yield a supernatant. The high salt solution may comprise any suitable salt, such as a sodium salt solution, and is used to substantially break up the HDL-phosvitin complex. A salt concentration of about 10% may be suitable. In one embodiment, the solution has a pH of about 7 and the solubilization takes place at a refrigerated temperature, about 4° C. in one example. Without being bound by any theory, it is believed that the use of a sodium salt solution such as NaCl causes the substitution of divalent calcium by monovalent sodium.

The resulting solubilized phosvitin/salt solution may be dialyzed against distilled water to reduce the salt concentration, if necessary or desired.

In one embodiment, phosvitin may be extracted without heating. The solubilized phosvitin/salt solution is collected, and the pH is adjusted to extract the phosvitin from HDLs, by precipitating non-phosvitin components such as the HDLs, and leaving the phosvitin in solution. As demonstrated in the Examples and in Table 1 (without heating), the purity of the recovered phosvitin increases as the pH for adjustment increases. In one embodiment, the pH is adjusted to about pH 5.0 or greater.

In one embodiment, the solubilized phosvitin/salt solution may be heated. In one embodiment, the supernatant from the protein granules-high salt solution is collected and heated at a temperature of about 80° C. for twenty minutes, and then dialyzed against double distilled water. The pH is then adjusted to extract the phosvitin from HDLs. As demonstrated in the Examples and in Table 2 (with heating), the purity of the recovered phosvitin is unaffected by pH; however, at pHs lower than pH 5.0, heat-treated phosvitin extracts show higher phosvitin recovery than that of unheated extracts. As further discussed below, heating appears to release more phosvitin from HDLs. In one embodiment, where the solubilized phosvitin is heated, the pH is adjusted to about pH 5.0 or lower.

In one embodiment, the pH of the solubilized phosvitin/salt solution may allow for recovery of the phosvitin without pH adjustment. As demonstrated in the Examples and in Tables 1 and 2, native pH (i.e., without pH adjustment) results in the highest recovery with reasonable purity.

After adjusting the pH in either one of the above embodiments (i.e., with or without heat treatment), the supernatant is centrifuged to yield a precipitate and supernatant comprising crude phosvitin. In one embodiment, centrifugation is conducted at 10,000×g for about twenty-five minutes. In one embodiment, centrifugation is conducted at a temperature of about 4° C. The crude phosvitin is then freeze-dried or lyophilized for use in various applications.

The purity of the phosvitin extract can be determined for example, by gel filtration HPLC using a commercial phosvitin standard (e.g., available from Sigma) to prepare a standard curve (Example 14). Recovery can be calculated, for example based on the ratio between phosvitin obtained from the method to the amount of phosvitin in the original egg yolk. As demonstrated in the Examples, the purity of the phosvitin obtained by the methods of the present invention appears to increase at decreasing pHs at the cost of recovery or yield; for example, a recovery of >100% with purity of 54.5% was obtained at native pH for unheated extract, and with greater purity (64% and 75%) for heated extracts.

In one embodiment, the protein granules may be solubilized at alkaline pHs, followed by isolation of phosvitin using anion exchange chromatography (Example 8). The phosvitin has a purity of 93% with a recovery yield of 57%.

In one embodiment, the purity of the phosvitin extract resulting from the methods of the present invention is in a range of about 50% to about 95%. In one embodiment, the purity is greater than about 75%, and preferably greater than about 80%. It is believed that the remaining non-phosvitin components primarily comprise HDLs such as lipovitellin.

In another aspect of the invention, the phosvitin extract may be used to prepare phosphopeptides. In one embodiment, the phosphopeptides of the present invention are produced from phosvitin using the methods described herein (Example 6). The method generally involves at least the steps of dephosphorylating the phosvitin and hydrolyzing the dephosphorylated phosvitin. The resultant hydrolysate comprises phosphopeptides which may have functional properties and suitability for particular applications such as, for example, as antioxidants, antibacterial or remineralizing agents, or improving mineral absorption in food, feed, cosmetic, dental and pharmaceutical products.

Phosvitin or an egg yolk fraction comprising phosvitin, such as that produced using the methods described or claimed herein, may be used as the starting material. In the process of bioactive peptide production, the limited enzymatic susceptibility of phosvitin can be considered as a major drawback; thus, the dephosphorylation of phosvitin by alkaline treatment increases the proteolytic susceptibility of phosvitin, and yields phosphopeptides after enzymatic digestion. In one embodiment, the phosvitin is treated with an alkaline solution at a sufficient time and temperature for dephosphorylation. In one embodiment, the alkaline solution is a solution of sodium hydroxide. The mixture is stirred for about half an hour at about room temperature. The pH may then be adjusted to about 8.0 using an acidic solution. In one embodiment, the acidic solution is a solution of hydrochloric acid.

The dephosphorylated phosvitin is then hydrolyzed with an enzyme such as trypsin, pancreatin, pepsin, thermolysin (from *Bacillus thermoproteolyticus rokko*), α-chymotrypsin (bovine pancreas), Protex 6L (from *Bacillus licheniformis*), Protex 30L (derived from *Bacillus subtilis*), or Protex 7L (from *Bacillus amyloliquefaciens*). In one embodiment, the enzyme comprises a digestive enzyme, under selected conditions of pH and temperature, to yield phosvitin phosphopeptides. In one embodiment, the enzyme comprises pancreatin. As used herein, the term "pancreatin" refers to a mixture of several digestive enzymes produced by the exocrine cells of the pancreas, and is composed of amylase, lipase and protease. In one embodiment, hydrolysis with pancreatin is conducted at an enzyme/substrate ratio of about 1:50 (w/w). In one embodiment, hydrolysis is conducted at a pH of about 8.0, and at a temperature of about 37° C. In one embodiment, hydrolysis is conducted for at least about three hours. If needed, the pH is adjusted to about 8.0 by adding an alkaline solution, such as sodium hydroxide. The hydrolysate solutions are then treated to inactivate the enzymes, such as by heat inactivation. In one embodiment, the hydrolysate solutions are heated at about 95° C. for about fifteen minutes. The hydrolysate solutions are then centrifuged to separate the soluble hydrolysates from non-soluble substances. In one embodiment, centrifugation is conducted at 10,000×g for about thirty minutes. In one embodiment, centrifugation is conducted at a temperature of about 4° C. The soluble hydrolysates may be freeze-dried for storage and future use.

The hydrolytic degradation of the phosvitin can be confirmed, for example, by gel filtration HPLC using a commercial phosvitin standard (e.g., available from Sigma) to prepare a standard curve (Example 14). The peptide/protein yield can be calculated, for example as the amount of protein in hydrolysate from 100 g yolk solids. The peptide/protein recovery can be calculated, for example as a percentage based on the weight ratio of amount of peptide/protein in the hydrolysate to the total protein in the egg yolk. As demonstrated in the Examples, egg yolk phosvitin was hydrolyzed by pancreatin to reach a degree of hydrolysis of 12.9% with a recovery of 6.1% based on egg yolk.

The soluble hydrolysates may be fractionated using anion exchange chromatography or ultra-filtration to yield one or more fractions. The properties of the fractions may be further analyzed by liquid chromatography coupled with tandem mass spectrometry (LC-MS/MS) to identify the peptides within the fractions.

In one embodiment, the soluble hydrolysates are fractionated using anion exchange chromatography to identify a fraction which the highest phosphorus content compared to any other fractions. In one embodiment, this fraction comprises at least one phosvitin or lipovitellin phosphopeptide comprising at least one phosphoserine residue.

In another aspect, the invention comprises pharmaceutical or nutraceutical compositions comprising a phosvitin extract, a phosvitin phosphopeptide or both in combination with one or more pharmaceutically acceptable carriers. Those skilled in the art are familiar with any pharmaceutically acceptable carrier that would be useful in this regard, and therefore the procedure for making pharmaceutical compositions in accordance with the invention will not be discussed in detail. Suitably, the pharmaceutical compositions may be in the form of tablets, capsules, liquids, lozenges, lotions, aerosol, and solutions suitable for various routes of administration including, but not limited to, orally, via injection or infusion, intraperitoneally, topically, nasally, ocularly, vaginally or rectally, in solid, semi-solid or liquid dosage forms as appropriate and in unit dosage forms suitable for easy administration of fixed dosages.

In one embodiment, the invention comprises a nutraceutical or a foodstuff comprising a phosvitin extract, a phosvitin phosphopeptide or both. A nutraceutical is a product isolated or purified from foods that is generally sold in medicinal forms not usually associated with foods. A nutraceutical generally has a physiological benefit or provides protection against disease. A foodstuff may be any compound or composition which is intended and suitable for human and/or animal consumption, including compounds and compositions which are consumed per se as well as compounds and compositions used as ingredients, components, and/or flavorings in other compositions.

It is well known to those skilled in the art that phosvitin and phosvitin phosphopeptides may provide potential health benefits, including antioxidant, anti-bacterial, metal chelating abilities, and calcium uptake into bones. In one embodiment, the invention comprises a method of providing a health benefit by administering to a subject a phosvitin extract, a phosvitin phosphopeptide or both, a pharmaceutical composition, a nutraceutical composition, a cosmetic product, a dental product or a foodstuff comprising the phosvitin extract, phosphopeptide or both, in an amount sufficient to effect any of the above health benefits.

The following is a specific example of one embodiment of the present invention. This example demonstrates one embodiment of the method of the present invention to extract phosvitin from egg yolk, and the production of phosphopeptides. This example is offered by way of illustration and is not intended to limit the invention in any manner.

High density lipoproteins (HDLs) have been reported to be soluble at alkaline pHs, insoluble at pH 7.5-7.8 for α-HDL and at pH 6.5-7.0 for β-HDL, but soluble at pH 4.5-5.0. In a report on the solubility between pH 5 to 7, the solubility of phosvitin was not affected, whereas HDLs were completely precipitated under pH 5.5 (Castellani et al., 2003). The isoelectric point of phosvitin was reported to be around pH 4 (Ternes, 1989). In view of such reports, the effect of pH upon the extraction of phosvitin was initially examined in order to determine whether phosvitin and HDLs might be separated by pH adjustments.

Figure 2:
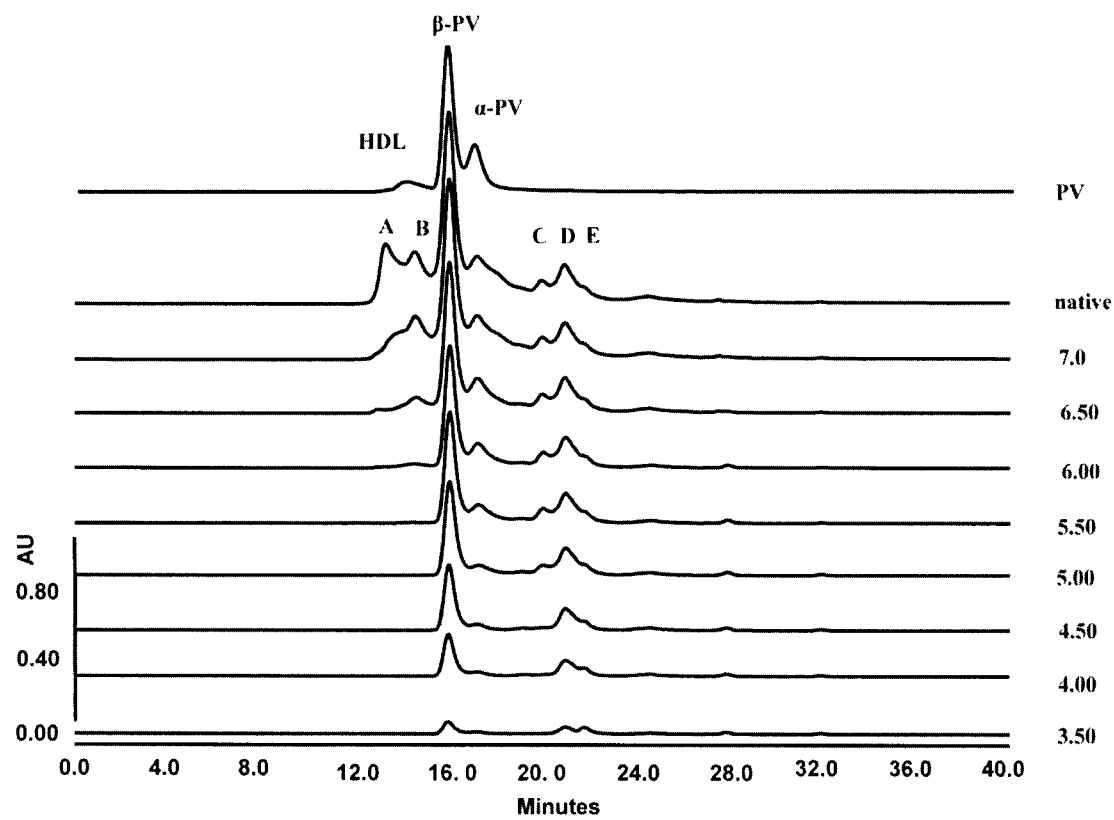
FIG. 2 shows gel filtration chromatograms of phosvitin extracts at different pHs (unheated). Absorbance was monitored at 215 nm.

Phosvitin extracts prepared at various pHs without heat treatment were analyzed by gel filtration chromatography (FIG. 2). Phosvitin prepared by different procedures is typically heterogeneous in gel filtration HPLC and electrophoresis (McBee and Cotterill, 1979; Abe et al., 1982; Wallace and Morgan, 1986a; Wallace and Morgan, 1986b). Standard phosvitin (Sigma) was fractionated into three major components. The first peak having a larger molecular weight is generally considered to represent HDL contaminant, while the other two peaks represent β-phosvitin (190 kDa) and α-phosvitin (160 kDa) (Tsutsui and Obaba, 1984).

The profile of the extract at native pH consisted of five components other than phosvitin. Fractions A and B may represent low density lipoprotein (LDL) and HDL respectively, accounting for 27.3% of the total protein. Fractions C, D and E may represent phosvettes or protein fractions from HDL or LDL based on the molecular weight, accounting for 15.4%. A shoulder peak in α-phosvitin probably suggests another contaminant in phosvitin. The phosvitin and contaminants tended to decrease at decreasing pHs. Fractions A and B decreased from 27.3% of total proteins to almost 0% at pH 3.5. Phosvitin purity first increased to 63.7% at pH 5.5, and then decreased to 39.6% at pH 3.5. Fractions C, D and E were not affected until reaching a pH lower than 5, where fraction C was eliminated. The proportion of these three fractions increased from 15.4% at native pH to 47.7% at pH 3.5.

The recovery, yield and purity of the phosvitin extract were compared against a commercial phosvitin standard (Sigma). As shown in Table 1, the purity of phosvitin extracts ranged from 39.6% to 63.7%. The best purity obtained was 63.7% at pH 5.5, with a recovery of 40.1%. The yield and recovery also decreased at decreasing pHs. The highest recovery was obtained at native pH, which was 109.60%, but was greatly decreased to 4.0% at pH 3.5. The fact that phosvitin's pI value is around 4.0 (Ternes, 1989) may explain the low recovery of phosvitin at low pH.

TABLE 1

Recovery and purity of phosvitin from egg yolk (without heating)

| pH | Purity (area %) | Phosvitin yield (g/100 g yolk solids) | Phosvitin recovery (4 g phosvitin in 100 g yolk solids) |
|---|---|---|---|
| Native | 54.5 ± 1.2 | 4.4 ± 0.1 | 109.6 ± 3.1 |
| 7.0 | 57.8 ± 3.1 | 3.8 ± 0.1 | 94.4 ± 2.1 |
| 6.5 | 61.2 ± 1.3 | 2.4 ± 0.2 | 60.2 ± 3.8 |
| 6.0 | 63.5 ± 0.2 | 1.9 ± 0.0 | 46.5 ± 1.0 |
| 5.5 | 63.7 ± 0.5 | 1.6 ± 0.0 | 40.1 ± 1.0 |
| 5.0 | 60.0 ± 0.3 | 1.2 ± 0.0 | 30.8 ± 0.9 |
| 4.5 | 56.6 ± 2.4 | 0.8 ± 0.0 | 20.9 ± 1.0 |
| 4.0 | 51.9 ± 4.6 | 0.5 ± 0.1 | 11.9 ± 1.4 |
| 3.5 | 39.6 ± 6.4 | 0.16 ± 0.0 | 4.0 ± 0.5 |

Figure 3:
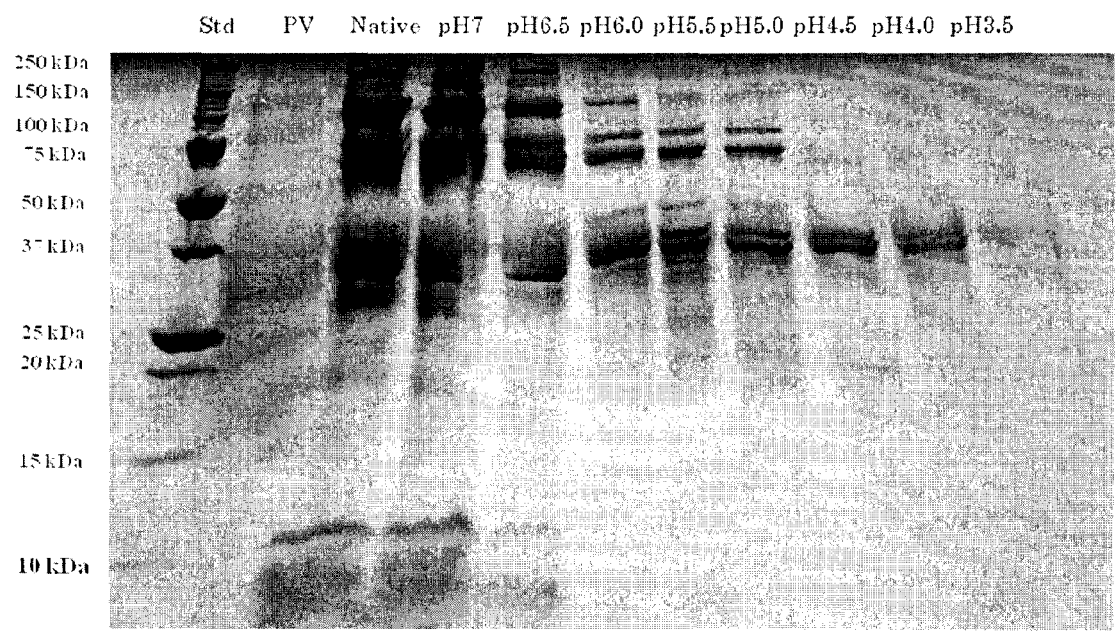
FIG. 3 is a photograph of a SDS-PAGE gel showing the protein profiles of phosvitin extracts prepared at different pHs without heating.

SDS-PAGE was used to analyze the composition of phosvitin extracts. The phosvitin standard has a molecular weight ranging from 30 kDa to 45 kDa as shown by SDS-PAGE (FIG. 3). The phosvitin extract at native pH has a major band within this range, as well as nine other bands having molecular weights of 240, 130, 80, 70, 35, 30, 25 and 20 kDa. These contaminating bands might arise from the large molecular weight fractions (A, B) and small molecular weight fractions (C, D, E) in HPLC. A significant decrease of the intensity of the large molecular weight bands was observed. The band at 240 kDa was absent at pH 6.0, which was inconsistent with the results of gel filtration chromatography. At pH 4.5, proteins bands with molecular weights of 130, 80, and 70 kDa were absent. Phosvitin was overlapped by other two protein bands having molecular weights of about 35 kDa. Without being bound by theory, these results suggest that high recovery (>100%) of phosvitin can be obtained at native pH with a purity of 54.5%. A decrease in pH can reduce large molecular weight contaminants, but also leads to loss in yield and recovery.

Figure 4:
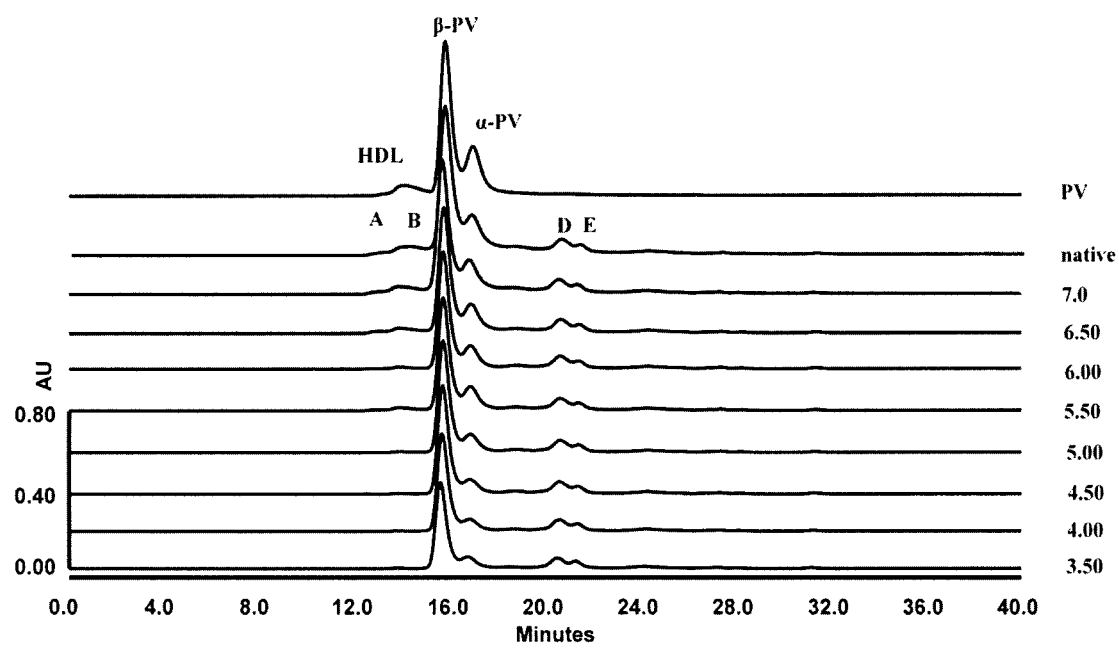
FIG. 4 shows gel filtration HPLC analysis of phosvitin at different pHs after heating.

Phosvitin is reportedly heat resistant since heating at 110° C. for twenty minutes does not cause aggregation or insolubility (Alberight et al., 1984). Anton et al. (2000) reported a great loss of HDLs' solubility upon heating granules at 79° C. in 0.5 M sodium chloride solution for about three minutes. The effect of heat treatment upon phosvitin purity and recovery was thus determined. After egg yolk protein granules were totally dissolved in 10% sodium chloride, the extraction solution was heated at 80° C. for twenty minutes. There appears to be less contaminant present in heated extracts compared to unheated extracts (FIG. 4). At the native pH, fractions A and B accounted for about 7.5%, while fractions D and E accounted for 10.5% of total protein. As the pH was lowered to 5.5, fractions A and B were no longer present. Fractions D and E accounted for 12.7% of total protein of the extract. Further lowering the pH to 3.5 did not eliminate fractions D and E. Without being bound by theory, these results suggest that heating reduced the solubility of HDL, thereby improving the separation of HDL from phosvitin.

The purity of heat-treated phosvitin extracts ranged from 75%-80%, which was significantly higher than the purity of unheated extracts (Table 2). The purity was unaffected by pH. The phosvitin yield and recovery were lower than those for unheated extracts at pH greater than 5.0. At pH lower than 5.0, heat-treated phosvitin extracts showed significantly higher phosvitin recovery than those of unheated extracts. Without being bound by theory, heating together with 10% sodium chloride extraction may more effectively denature HDL and break the phosphocaleic bridge to release more phosvitin from HDL. HDL precipitated when the pH was lowered, but phosvitin remained in the extracts. With heat treatment, recovery and purity of the phosvitin extracts improved.

TABLE 2

Recovery and purity of phosvitin from egg yolk (with heating)

| pH | Purity (area %) | Phosvitin yield (g/100 g yolk solids) | Phosvitin recovery (4 g phosvitin in 100 g yolk solids) |
|---|---|---|---|
| Native | 75.7 ± 1.0 | 2.6 ± 0.1 | 64.2 ± 2.4 |
| 7.0 | 76.2 ± 0.5 | 2.2 ± 0.1 | 54.5 ± 2.2 |
| 6.5 | 76.7 ± 0.3 | 1.8 ± 0.1 | 45.3 ± 2.0 |
| 6.0 | 78.6 ± 0.1 | 1.6 ± 0.1 | 40.3 ± 1.7 |
| 5.5 | 79.7 ± 0.7 | 1.6 ± 0.0 | 39.0 ± 0.1 |
| 5.0 | 80.1 ± 1.0 | 1.6 ± 0.1 | 38.9 ± 2.0 |
| 4.5 | 79.5 ± 1.2 | 1.4 ± 0.0 | 33.9 ± 0.2 |
| 4.0 | 79.1 ± 1.3 | 1.2 ± 0.1 | 30.7 ± 1.3 |
| 3.5 | 79.3 ± 1.3 | 1.1 ± 0.1 | 28.6 ± 2.3 |

Figure 5:
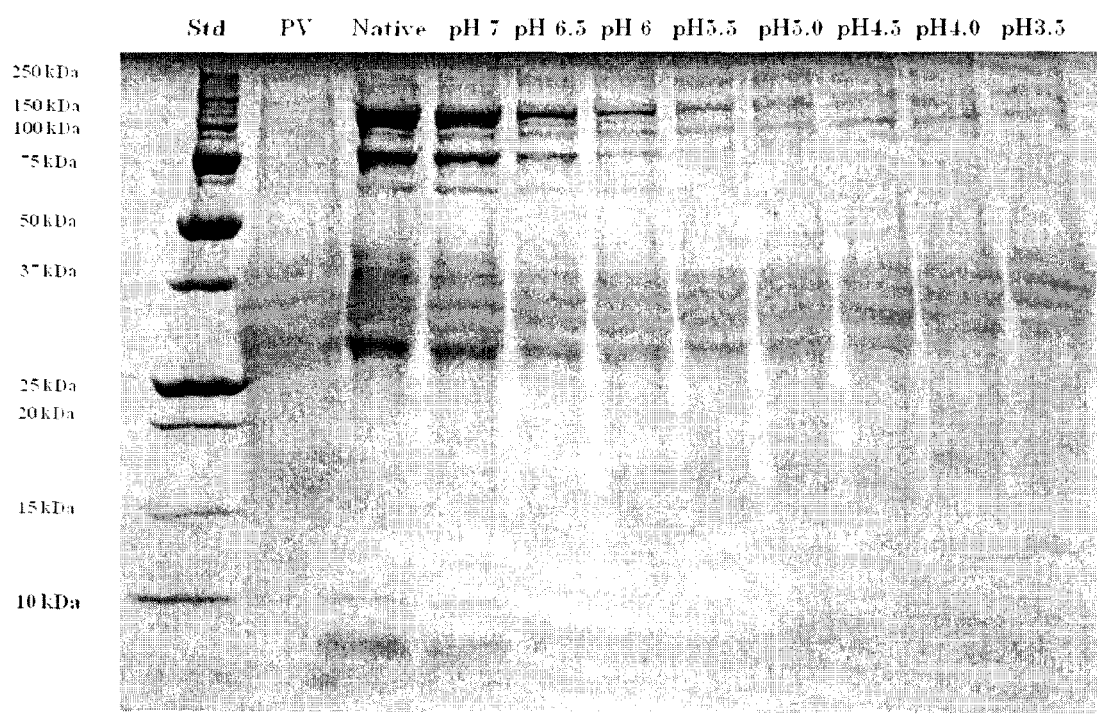
FIG. 5 is a photograph of a SDS-PAGE gel showing the protein profiles of phosvitin extracts at different pHs with heating.

FIG. 5 shows the SDS-PAGE profile of phosvitin extracts at different pHs (with heating). The phosvitin extract at native pH was resolved into nine proteins subunits, with molecular weights of 130, 100, 80, 70, 45, 40, 35, 30 and 10 kDa. The standard phosvitin (Sigma) was resolved into two bands, with molecular weights of 35 and 30 kDa, respectively. In HPLC, the large molecular weight fractions A and B were absent at around pH 6.0. In SDS-PAGE, a significant reduction of protein bands with molecular weights of 130, 80 and 10 kDa at this pH was observed. From pH 5 and below, there were only two minor contaminants at molecular weights of 130 and 100 kDa. These results concur with the results of HPLC analysis. Based upon these results, heating at 10% sodium chloride extraction may improve the phosvitin purity from 63.7% to 80.1% (optimum purity of both experiments), whereas recovery decreased from 109.6% to 64.2%.

Figure 9:
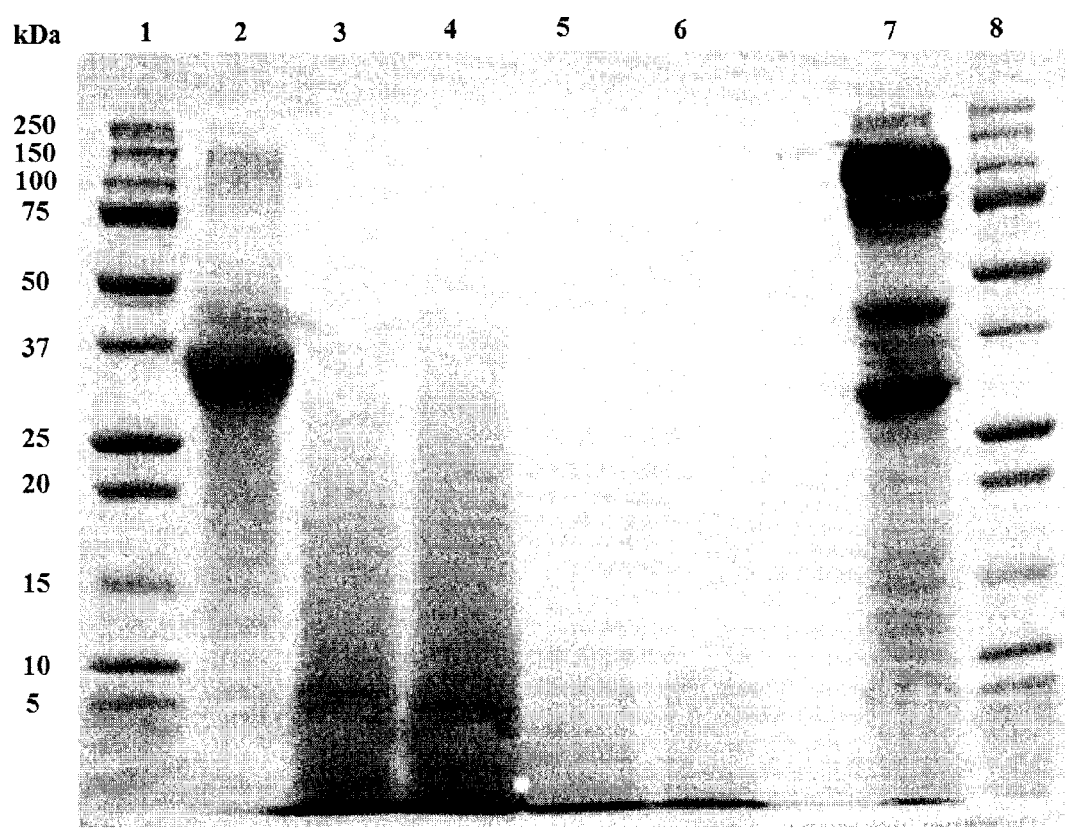
FIG. 9 is a photograph of a SDS-PAGE gel showing the protein profiles of pancreatin hydrolysates of granules and extracted phosvitin (both granules and phosvitin were dephosphorylated by 0.2 M NaOH for 0.5 h before hydrolysis). 1 and 8, molecular weight markers; 2, phosvitin standard; 3 and 4, pancreatin hydrolysates of granules; 5 and 6, pancreatin hydrolysates of purified phosvitin; 7, egg yolk granules.

The production of phosvitin phosphopeptides comprises the steps of dephosphorylation and hydrolysis. As shown in FIG. 9, no phosvitin or large molecular weight proteins were detected in phosvitin hydrolysate. It has been reported that without dephosphorylation, hydrolysis of phosvitin by pepsin, trypsin and α-chymotrypsin produces only two to four small fractions from the C- and N-termini, leaving one major fraction of 28-29 kDa as phosvitin core (Goulas et al., 1996; Khan et al., 1998; Jiang and Mine, 2000; Wallace and Morgan, 1986). Only two bands were detected at 6.5 kDa and 3.5 kDa (FIG. 9, lanes 5 and 6).

Figure 10:
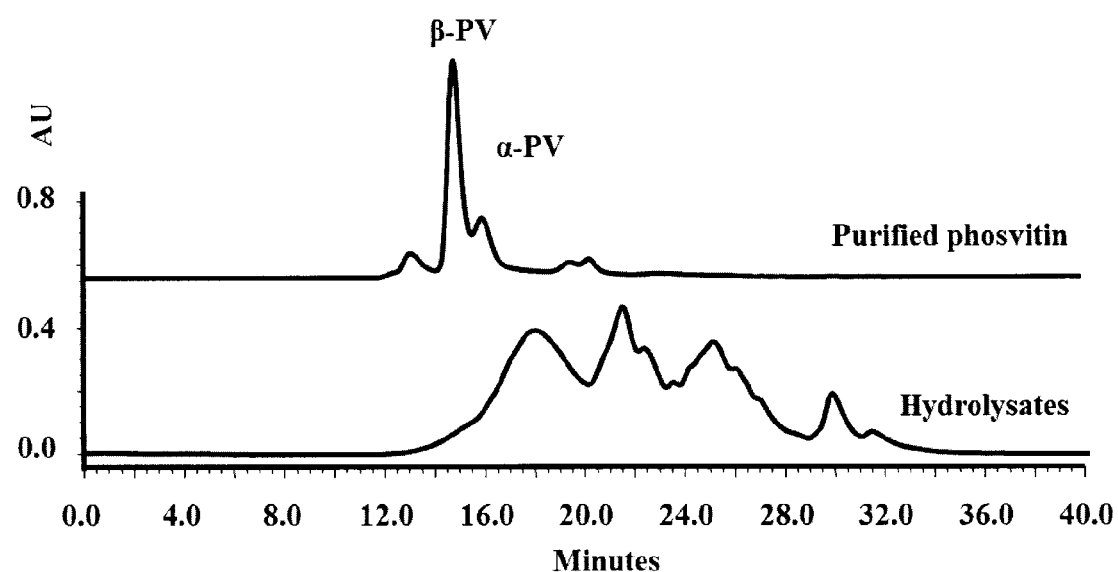
FIG. 10 shows the HPLC elution profiles of granules, extracted phosvitin and their hydrolysates.

As shown in FIG. 10, gel filtration chromatography indicated that phosvitin can be degraded after dephosphorylation. The two phosvitin peaks, α- and β-phosvitin, were degraded into smaller fractions.

In one embodiment, the phosvitin is hydrolyzed to a degree of hydrolysis greater than about 6%, and preferably greater than about 10%. In one embodiment, the degree of hydrolysis (DH), recovery and yield are summarized in Table 3. The DH of phosvitin using pancreatin after dephosphorylation was 12.9%, which exceeds a reported DH of 5.2% (Chay Pak Ting et al., 2011).

In one embodiment, the hydrolysate has a nitrogen to phosphorus (N/P) of less than about 5, and preferably less than about 4. It is preferable to have a low N/P ratio for phosphopeptides. In one embodiment, the N/P ratio of phosvitin hydrolysate was 3.9, which is lower than both purified casein phosphopeptides with the N/P ratio ranging from 6 to 8 (Peterson et al., 1958; Bennich et al., 1959) and the phosvitin hydrolysate with the N/P ratio of 11.8 (Chay Pak Ting et al., 2011).

TABLE 3

Degree of hydrolysis, protein yield, protein recovery and N/P value of pancreatin-digested phosvitin

| Pancreatin hydrolysis | DH % | Protein yield mg/g wet yolk | Protein recovery from egg yolk % | N/P atomic ratio |
|---|---|---|---|---|
| phosvitin | 12.9 ± 3.1 | 10.4 ± 0.3 | 6.1 ± 0.2 | 3.9 ± 0.1 |

Figure 11:
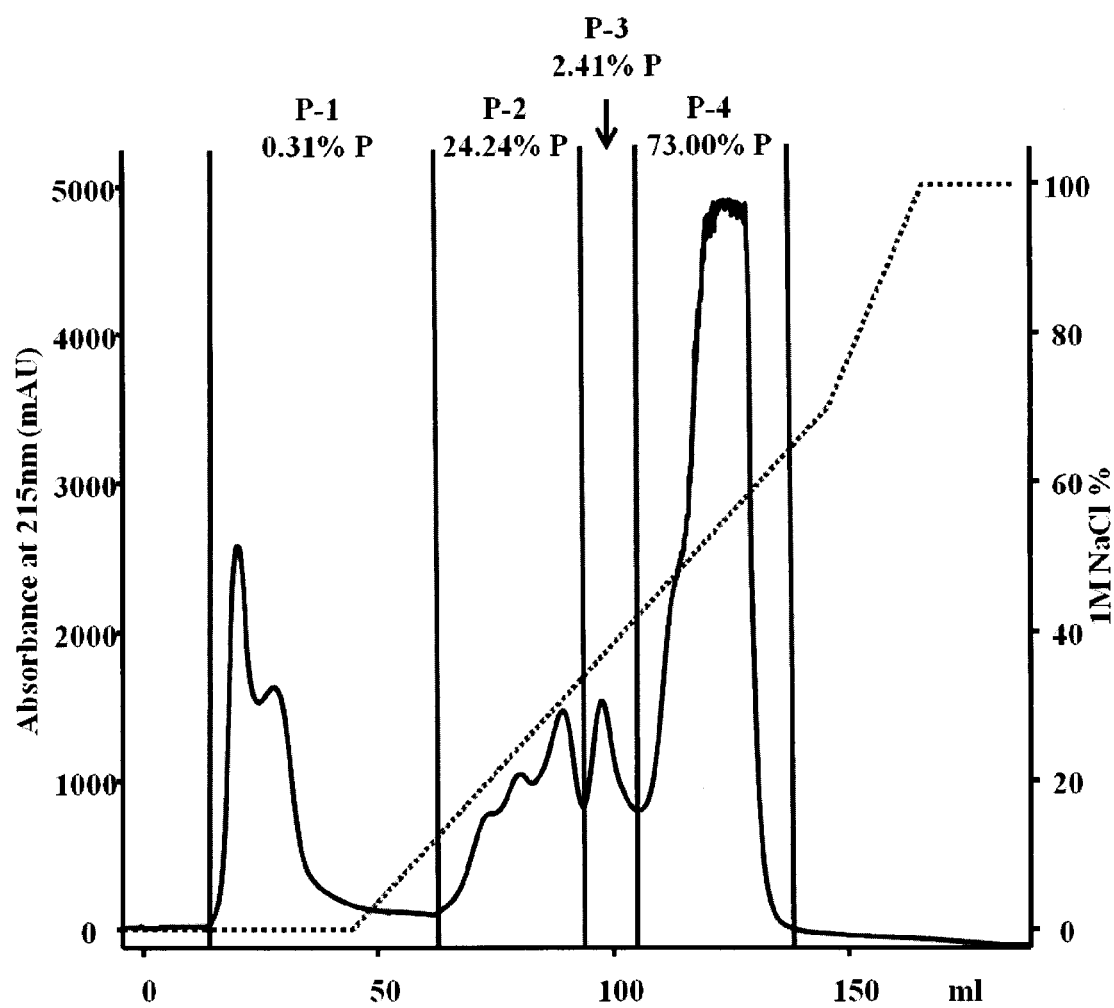
FIG. 11 shows the elution profile of anion exchange chromatography of pancreatin hydrolysates of extracted phosvitin.
Figure 12A:
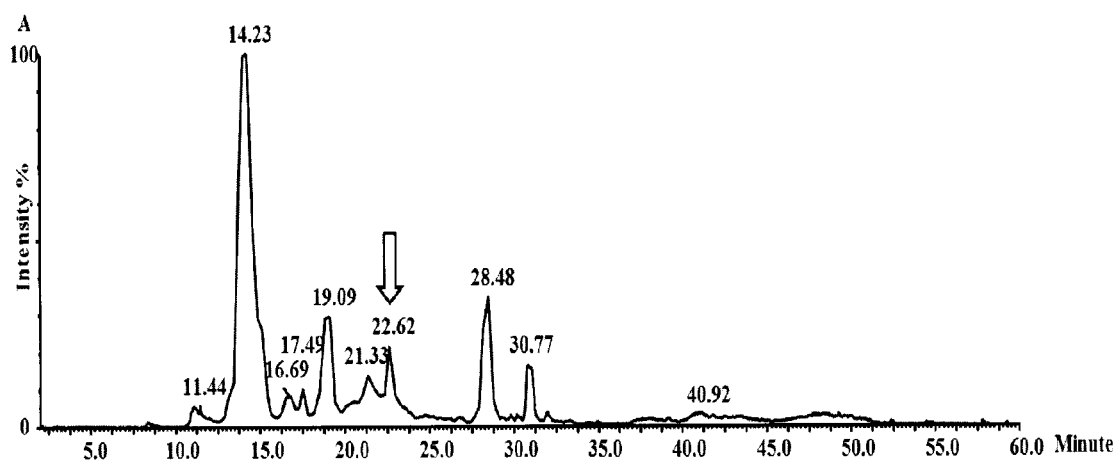
FIGS. 12A-C show the results of de novo sequencing of one representative peptide LEDDSSSSSSSSVLSK (SEQ ID NO: 30) with 9 phosphate groups from fraction P-4 by using MS/MS spectra.
Figure 12B:
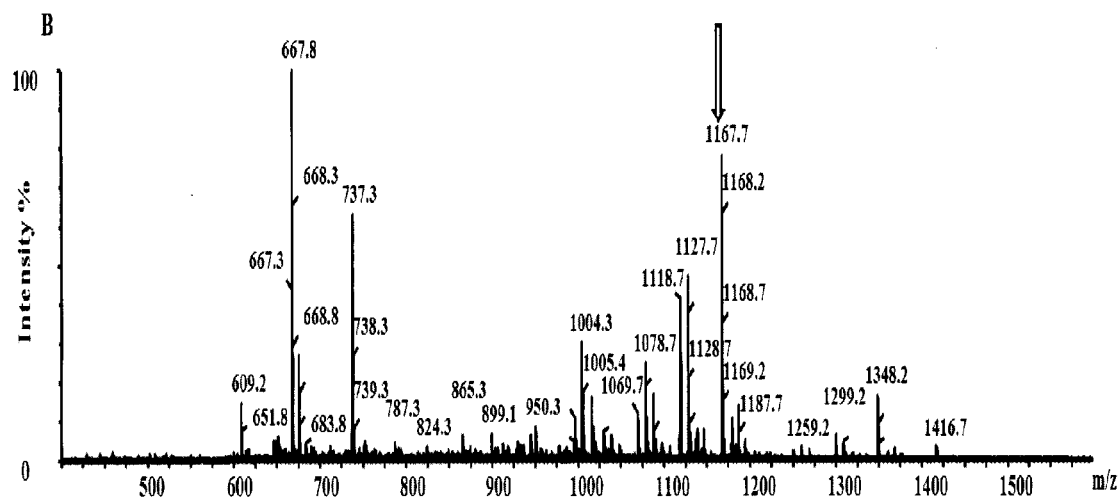
Figure 12C:
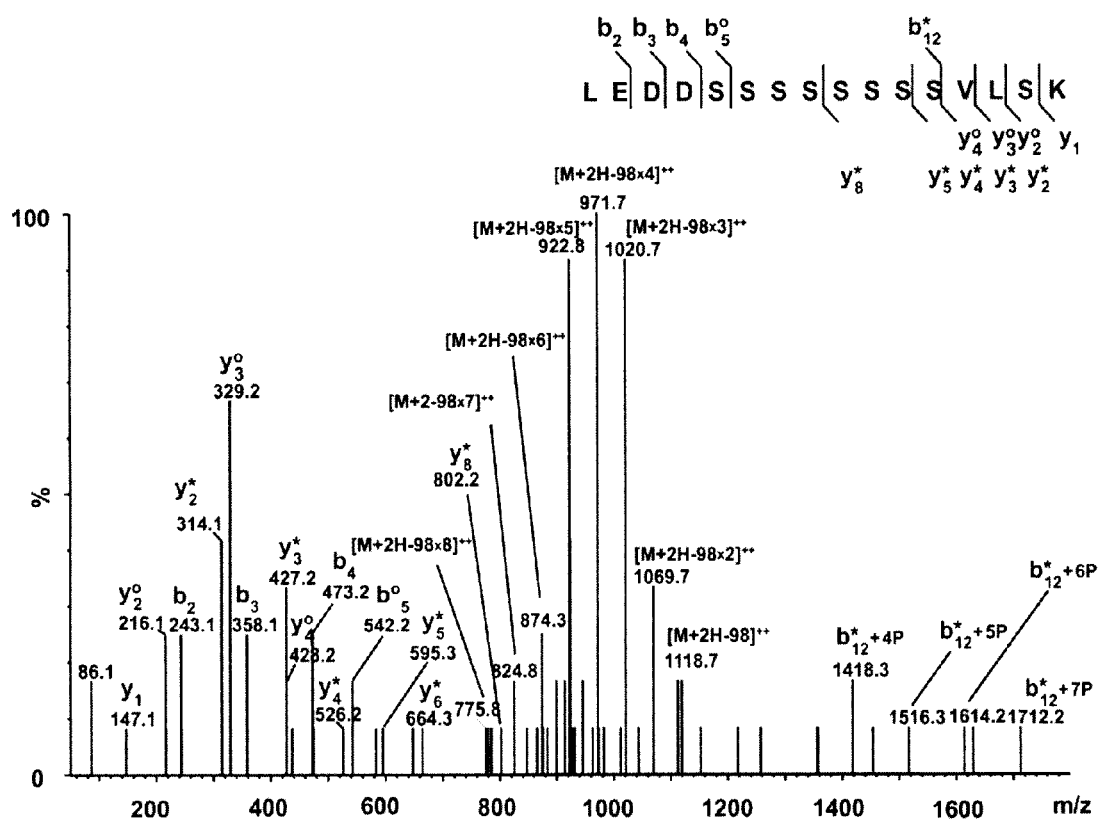

Phosvitin hydrolysate was fractionated by an anion exchange column, resulting in four fractions representing 0.3%, 24.2%, 2.4% and 73.0% of the total phosphorus content (FIG. 11). The last fraction P-4 exhibiting the highest phosphorus content was either dephosphorylated with phosphatase or used directly for structural characterization (FIGS. 12A-C).

Thirty-two peptides were identified from fraction P-4 derived mainly from three phosvitin domains: AEFGTEPDAKTSSSSSSASSTATSSSSSSASSPN (PV 1-34; SEQ ID NO: 1), KPMDEEENDQV (PV 37-47; SEQ ID NO: 9) and SGHLEDDSSSSSSSSVLSKIWG (PV 190-211; SEQ ID NO: 14); and six peptides were identified from one lipovitellin domain: IITEVNPESEEEDESSPYEDI (VTG 1056-1076; SEQ ID NO: 36) (Table 4). Peptides with 6-10 phosphate groups were identified from domain PV 190-211 (SEQ ID NO: 14). Although no phosphorylation was identified in the peptides derived from domain PV 1-34 (SEQ ID NO: 1), it was possible that phosphopeptides may have been generated but could not be retained by the dC-18 column prior to MS/MS analysis. Young et al. (2011) reported phosvitin peptides from three domains: PV 4-40, PV 155-197 and PV 244-257. PV 4-40 and PV 244-257 partially overlapped with the domains detected herein. The last domain PV 244-257 (EDDSSSSSSSSVLSKIWGRHEIYQ; SEQ ID NO: 38) overlapped with the domain PV 190-211 detected herein. Phosvitin contains 217 total amino acids (Byrne et al., 1984; Goulas et al., 1996). Peptides from the domain PV 155-197 were not detected. Without being bound by theory, this result may be due to the different enzymes which were used (i.e., pancreatin versus trypsin). Young et al. (2011) reported only two phosphorylated peptides out of thirteen peptides with one and three phosphate groups, although the same group previously reported that the peptides prepared contained 18.9% phosphorus (Katayama et al., 2006).

As summarized in Table 4, five phosphorylated peptides were identified containing six to ten phosphate groups (SEQ ID NOS: 17, 24, 27, 30 and 33). Peptides with the same amino acid sequences might contain different numbers of phosphate groups. Peptide sequences identified from native and dephosphorylated peptides were combined together. Sequences including bold letters were found in both native and dephosphorylated peptides. Sequences including italic letters were found in both phosvitin hydrolysate and granules hydrolysate. M/Z values were obtained by mass spectrometry. Mr (expt) is the determined molecular mass of the peptides, and Mr (calc) is the theoretical mass of the closest matching peptides. Phosphorylation was identified from native peptides without dephosphorylation. In some cases, one peptide contains a different number of phosphate groups. The smallest peptides from each domain comprised 8, 9 or 10 consecutive amino acid residues.

TABLE 4

Peptides identified in anion exchange chromatography fraction P-4 (pancreatin hydrolysate of extracted phosvitin)

| | Position | Sequence | M/Z | Z | Mr (Expt) | Mr (Calc) |
|---|---|---|---|---|---|---|
| Domain I | 1112-1145 | AEFGTEPDAKTSSSSSASSTATSSSSSSASSPN (PV 1-34; SEQ ID NO: 1) | | | | |
| 1 | 1115-1133 | GTEPDAKTSSSSSSASSTA (SEQ ID NO: 2) | 879.4 | 2 | 1756.8 | 1756.8 |
| 2 | 1112-1120 | AEFGT(P)EPDA (SEQ ID NO: 3) | 936.4 | 1 | 935.4 | 935.4 |
| 3 | 1112-1131 | AEFGTEPDAKTSSSSSSASS (SEQ ID NO: 4) | 966.9 | 2 | 1931.9 | 1931.8 |
| 4 | 1112-1119 | *AEFGTEPD* (SEQ ID NO: 5) | 865.4 | 1 | 864.4 | 864.4 |
| 5 | 1120-1145 | *AKTSSSSSSASSTATSSSSSSASSPN* (SEQ ID NO: 6) | 1169.5 | 2 | 2337.1 | 2337.0 |
| 6 | 1115-1145 | GTEPDAKTSSSSSSASSTATSSSSSSASSPN (SEQ ID NO: 7) | 1419.1 | 2 | 2836.2 | 2836.2 |
| 7 | 1122-1145 | *TSSSSSSASSTATSSSSSSASSPN* (SEQ ID NO: 8) | 1070.0 | 2 | 2137.9 | 2137.9 |
| Domain II | 1148-1158 | KPMDEEENDQV (PV 37-47; SEQ ID NO: 9) | | | | |

TABLE 4-continued

Peptides identified in anion exchange chromatography fraction P-4 (pancreatin hydrolysate of extracted phosvitin)

|   | Position | Sequence | M/Z | Z | Mr (Expt) | Mr (Calc) |
|---|----------|----------|-----|---|-----------|-----------|
| 8 | 1148-1158 | KPMDEEENDQV (SEQ ID NO: 10) | 667.3 | 2 | 1332.6 | 1332.6 |
| 9 | 1151-1158 | *DEEENDQV* (SEQ ID NO: 11) | 489.2 | 2 | 976.4 | 976.4 |
| 10 | 1148-1157 | KPMDEEENDQ (SEQ ID NO: 12) | 667.3 | 2 | 1332.6 | 1332.6 |
| 11 | 1150-1158 | MDEEENDQV (SEQ ID NO: 13) | 554.7 | 2 | 1107.4 | 1107.4 |
| Domain III | 1301-1322 | SGHLEDDSSSSSSSSVLSKIWG (PV 190-211; SEQ ID NO: 14), 6-10 phosphorylation** | | | | |
| 12 | 1308-1320 | SSSSSSSVLSKI (SEQ ID NO: 15) | 628.3 | 2 | 1254.6 | 1254.6 |
| 13 | 1306-1318 | DDSSSSSSSSVLS (SEQ ID NO: 16) | 622.8 | 2 | 1243.5 | 1243.5 |
| 14 | 1301-1319 | SGHLEDDSSSSSSSSVLSK (10P; SEQ ID NO: 17) | 948.4 | 2 | 1894.9 | 1894.8 |
| 15 | 1307-1319 | *DSSSSSSSSVLSK* (SEQ ID NO: 18) | 629.3 | 2 | 1256.6 | 1256.6 |
| 16 | 1304-1317 | *LEDDSSSSSSSSVL* (SEQ ID NO: 19) | 700.3 | 2 | 1398.6 | 1398.6 |
| 17 | 1306-1319 | *DDSSSSSSSSVLSK* (SEQ ID NO: 20) | 1372.6 | 1 | 1371.6 | 1371.6 |
| 18 | 1307-1320 | *DSSSSSSSSVLSKI* (SEQ ID NO: 21) | 685.8 | 2 | 1369.7 | 1369.7 |
| 19 | 1312-1320 | SSSSVLSKI (SEQ ID NO: 22) | 454.3 | 2 | 906.5 | 906.5 |
| 20 | 1310-1320 | SSSSSSVLSKI (SEQ ID NO: 23) | 541.3 | 2 | 1080.6 | 1080.6 |
| 21 | 1301-1318 | SGHLEDDSSSSSSSSVLS (8P; SEQ ID NO: 24) | 884.4 | 2 | 1766.8 | 1766.7 |
| 22 | 1305-1322 | EDDSSSSSSSSVLSKIWG (SEQ ID NO: 25) | 929.4 | 2 | 1856.8 | 1856.8 |
| 23 | 1304-1322 | LEDDSSSSSSSSVLSKIWG (SEQ ID NO: 26) | 986.0 | 2 | 1969.9 | 1969.9 |
| 24 | 1301-1320 | SGHLEDDSSSSSSSSVLSKI (6-7P; SEQ ID NO: 27) | 1005.0 | 2 | 2007.9 | 2007.9 |
| 25 | 1306-1320 | *DDSSSSSSSSVLSKI* (SEQ ID NO: 28) | 1485.7 | 1 | 1484.7 | 1484.7 |
| 26 | 1304-1318 | *LEDDSSSSSSSSVLS* (SEQ ID NO: 29) | 743.8 | 2 | 1485.6 | 1485.6 |
| 27 | 1304-1319 | LEDDSSSSSSSSVLSK (7, 8, 9P; SEQ ID NO: 30) | 807.9 | 2 | 1613.7 | 1613.7 |
| 28 | 1307-1322 | DSSSSSSSSVLSKIWG (SEQ ID NO: 31) | 807.4 | 2 | 1612.8 | 1612.8 |
| 29 | 1301-1317 | SGHLEDDSSSSSSSSVL (SEQ ID NO: 32) | 840.9 | 2 | 1679.7 | 1679.7 |
| 30 | 1304-1320 | LEDDSSSSSSSSVLSKI (7P; SEQ ID NO: 33) | 864.4 | 2 | 1726.8 | 17268. |

TABLE 4-continued

Peptides identified in anion exchange chromatography fraction P-4 (pancreatin hydrolysate of extracted phosvitin)

| | Position | Sequence | M/Z | Z | Mr (Expt) | Mr (Calc) |
|---|---|---|---|---|---|---|
| 31 | 1306-1317 | DDSSSSSSSSVL (SEQ ID NO: 34) | 1157.5 | 1 | 1156.5 | 1156.5 |
| 32 | 1306-1322 | DDSSSSSSSSVLSKIWG (SEQ ID NO: 35) | 864.9 | 2 | 1727.8 | 1727.8 |
| Domain IV | 1056-1076 | IITEVNPESEEEDESSPYEDI (lipovitellin; SEQ ID NO: 36) | | | | |
| 33 | 1056-1072 | *IITEVNPESEEEDESSP* (SEQ ID NO: 37) | 952.4 | 2 | 1902.8 | 1902.8 |
| 34 | 1060-1076 | *VNPESEEEDESSPYEDI* (SEQ ID NO: 38) | 984.4 | 2 | 1966.8 | 1966.8 |
| 35 | 1059-1076 | *EVNPESEEEDESSPYEDI* (SEQ ID NO: 39) | 1048.9 | 2 | 2095.8 | 2095.8 |
| 36 | 1068-1076 | DESSPYEDI (SEQ ID NO: 40) | 1054.4 | 1 | 1053.4 | 1053.4 |
| 37 | 1059-1072 | *EVNPESEEEDESSP* (SEQ ID NO: 41) | 788.8 | 2 | 1575.6 | 1575.6 |
| 38 | 1060-1073 | VNPESEEEDESSPY (SEQ ID NO: 42) | 805.8 | 2 | 1609.6 | 1609.6 |

Exemplary embodiments of the present invention are described in the following Examples, which are set forth to aid in the understanding of the invention, and should not be construed to limit in any way the scope of the invention as defined in the claims which follow thereafter.

Example 1

Reagents

Sodium chloride, sodium hydroxide, and hydrochloric acid were purchased from Fisher Scientific (Nepean, ON, Canada). Glycine, Precision Plus™ Protein Standard, sodium dodecyl sulfate (SDS), and precast gel (10-20% Tris-HCl) were purchased from Bio-Rad Laboratories, Inc. (Hercules, Calif., USA). Phosvitin standard (P1253, from chicken egg yolk) from chicken egg yolk was purchased from Sigma-Aldrich Ltd. (Oakville, ON, Canada). The deionized distilled water used for all the experiments and was produced by a Barnstead™ water purification system (Thermo Fisher Scientific, Waltham, Mass., USA). Trypsin (T4799-10G, from porcine pancreas), pancreatin (p7545-25G, from porcine pancreas), pepsin (p7000-25G, from porcine gastric mucosa), thermolysin (p1512-25MG, from *Bacillus thermoproteolyticus rokko*) and α-chymotrypsin (c4129-1G, from bovine pancreas) were purchased from Sigma-Aldrich, Ltd. (Oakville, ON, Canada). Protex 6L (4880883444, from *Bacillus licheniformis*), Protex 30L (4880873541, derived from *Bacillus subtilis*) and Protex 7L (4860881508, derived from *Bacillus amyloliquefaciens*) were purchased from Danisco US Inc. (Rochester, N.Y., USA). All the other chemicals were purchased from Sigma-Aldrich, Ltd. (Oakville, ON, Canada) or Fisher Scientific (Nepean, ON, Canada) unless otherwise specified.

Example 2

Preparation of Egg Yolk

Eggs were purchased from a local supermarket on the day of the experiment. For each egg, the shell was manually broken, and the yolk was separated from the egg white and rolled on Whatman™ filter paper (Whatman Inc., Florham Park, N.J.) to remove albumen and chalazes adhering to the vitellin membrane. This membrane was then perforated to collect unspoiled egg yolk in a beaker cooled in iced water.

Example 3

Preparation of Protein Granules

Protein granules were obtained as described by McBee and Cotterill (1979) with slight modifications. Yolk was twice diluted with deionized water, and mixed by magnetic stirring for one hour at 4° C. The mixture was centrifuged at 10,000 g for forty-five minutes at 4° C. The precipitate (i.e., protein granules) was collected for phosvitin preparation.

Example 4

Phosvitin Preparation

The protein granules were re-suspended in 10% sodium chloride, maintaining a pH of 7.25 at 4° C. The solution was collected and divided into several beakers for pH experiments. The pH of the aliquots was adjusted to 7, 6.5, 6.0, 5.5, 5.0, 4.5, 4.0 and 3.5, and the supernatant was stirred with magnetic stirring for one hour, followed by centrifugation at 10,000×g at 4° C. for twenty-five minutes. The precipitate was removed and the supernatant containing phosvitin was filtered through a 0.22 μm membrane for HPLC analysis.

Example 5

Phosvitin Preparation with Heat Treatment During NaCl Extraction

The protein granules were re-suspended in 10% sodium chloride, maintaining the pH at 7.25. The solution was first heated at 80° C. for twenty minutes, and then dialyzed against double distilled water. The steps which follow are the same as described in Example 4 for phosvitin preparation. Samples at different pHs were analyzed by gel filtration HPLC.

Example 6

Anion Exchange Chromatography

The precipitate (i.e., the protein granules) was collected and re-suspended in 0.05 M carbonate-bicarbonate buffer (pH 9.6). Granules were completely dissolved after one to two hours of magnetic stirring. The granule solution was filtered through a 0.22 μm filter. Samples were loaded to a HiPrep™ Q FF 16/10 anion exchange column (GE Healthcare Life Sciences, USA). The column was equilibrated in advance with 0.05 M carbonate-bicarbonate buffer pH 9.6. The chromatographic elution was run by an AKTA-FPLC system (GE Healthcare Biosciences, Pittsburgh, Pa., USA) at a flow rate of 2 mL/min, with buffer A being 0.05 M carbonate-bicarbonate buffer (pH 9.6), and buffer B being 0.5 M sodium chloride in buffer A. The column was first run for six bed volumes, with increasing buffer B from 0% to 45%, and then to 75% in twenty bed volumes. The effluent was monitored at 280 nm.

Figure 6:
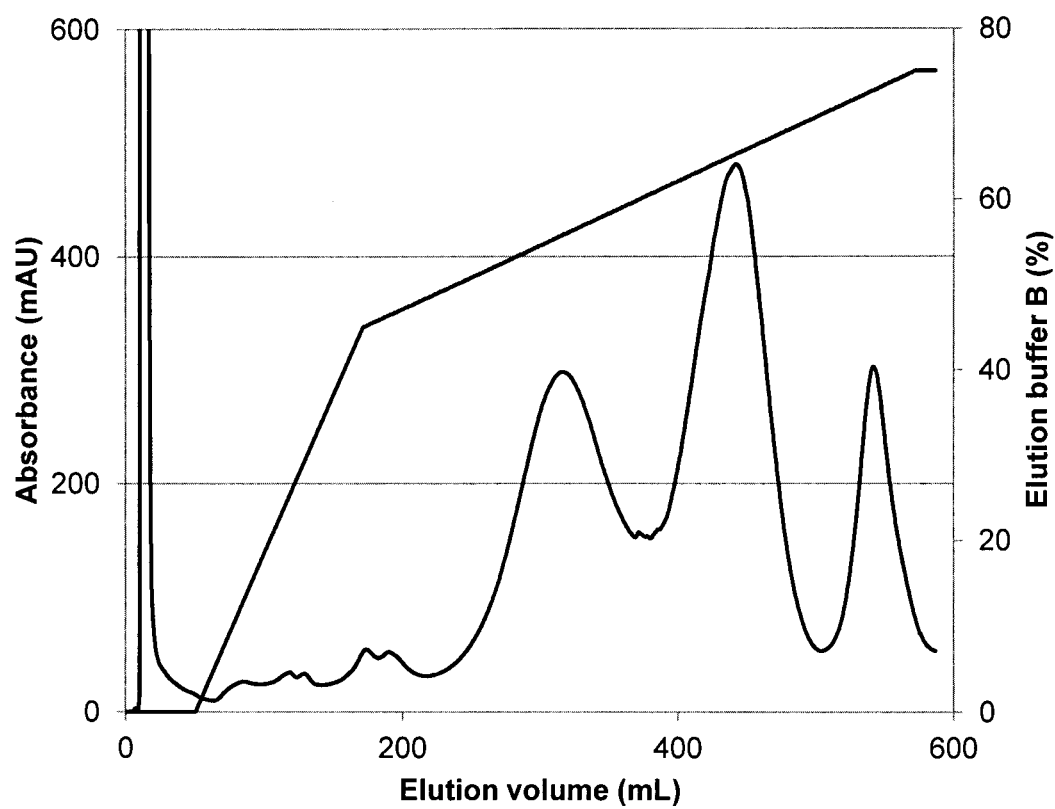
FIG. 6 shows the elution profile of anion exchange chromatography of dissolved granule solution prepared from egg yolk.

Prepared granules were dissolved in 0.05 M carbonate-bicarbonate buffer (pH 9.6), and loaded onto an anion exchange column (FIG. 6). Three well resolved peaks eluted from the column at 315, 442, and 542 ml, which accounted for 20, 32, and 11% (w/w) of the loaded amount, apart from 36% (w/w) of loaded amount which passed through the column as unbound.

Figure 7:
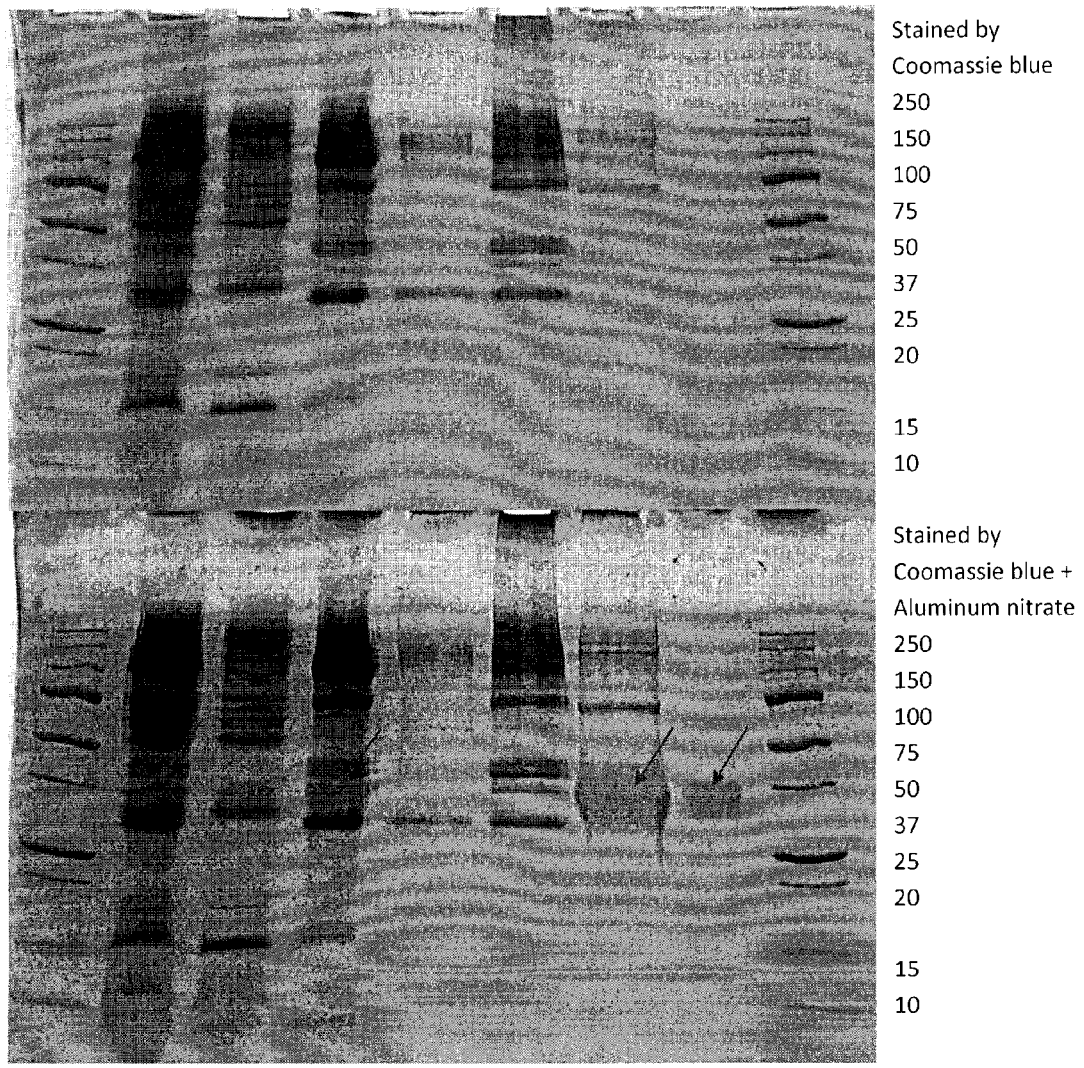
FIG. 7 is a photograph of a SDS-PAGE gel showing the protein profiles of three peaks eluted from anion exchange column loaded with granule solution in 0.05 M carbonate-bicarbonate buffer at pH 9.6, comparing with egg yolk, plasma, granules and phosvitin standard (Sigma, "PVT Std").

The eluted peaks were analyzed by native SDS-PAGE against phosvitin standard (FIG. 7). The gel was first stained using Coomasssie brilliant blue, which shows no phosvitin bands (upper gel). The gel was then again stained using Coomassie brilliant blue and aluminum nitrate (lower gel). Phosvitin bands were observed in yolk, granules and peak 3 at position around 37 kDa (arrows). Standard phosvitin (Sigma) has a molecular weight of 34 kDa. These results indicated that phosvitin was successfully isolated from granules by an anion exchange column. Peak 2 was mainly HDL as compared with the granules band (data not shown). Anion exchange chromatography was very effective in fractionating phosvitin from the granule solution.

Figure 8:
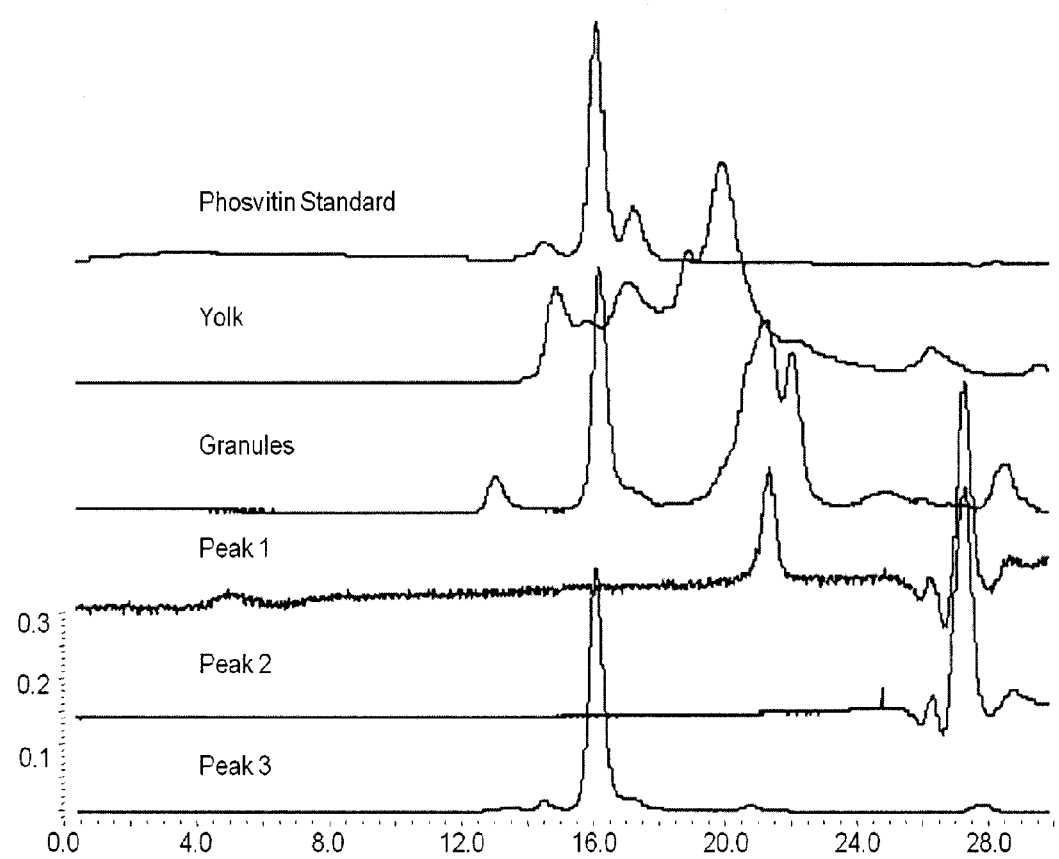
FIG. 8 shows the HPLC elution profiles of different fractions during phosvitin purification from egg yolk.

Gel filtration HPLC analysis further showed peak 3 has a calculated purity of 93% against standard phosvitin, at a recovery of 57.7% (FIG. 8).

Example 7

Dephosphorylation and Hydrolysis of Phosvitin

Lyophilized phosvitin extract was dephosphorylated in 0.2 M NaOH at room temperature (25° C.) for 0.5 hours. After adjusting the pH of slurry to 8.0 with 3 M HCl, pancreatin was added at a ratio of 1/50 (enzyme/phosvitin, w/w). Incubation was carried out in a 100 mL jacket beaker at constant temperature of 37° C. for 3 hours, and the pH was maintained constant during the incubation by adding of 0.2 M NaOH if necessary. To terminate the enzymatic reactions, the temperature was raised to 95° C. and held for 15 minutes. Hydrolysates were centrifuged at 10,000×g for 30 minutes at 4° C. and lyophilized.

Example 8

Molecular Weight (MW) Distribution of Hydrolysates

A Superdex™ peptide 10/300 GL column (GE Healthcare, Piscataway, N.J., USA) was used to determine the molecular weight distribution of hydrolysates on an AKTA™ Explorer 10S system (GE Healthcare, Piscataway, N.J., USA). Samples prepared at 0.5 mg/ml in 30% aqueous acetonitrile containing 0.1% trifloroacetic acid were injected into the column at a volume of 100 μl, and eluted with the same buffer. Elution was monitored at 215 nm. Molecular weights were calculated according to a calibration curve created by running molecular weight markers under identical conditions.

Pancreatin hydrolysate from granules and phosvitin were prepared at 15 mg/mL with buffer A (0.05M Tris-HCl at pH 8.0) and filtered through a 0.45 μm membrane (Millipore, Billerica, Mass., USA) before loading to the HiPrep 16/10 Q FF anion exchange column. The elution was monitored at 215 nm and operated by the AKTA Explorer 10S system (GE Healthcare, Piscataway, N.J., USA) from 100% buffer A to 100% buffer B (1.0 M NaCl in buffer A). Fractions were collected and lyophilized for analysis.

Example 9

Dephosphorylation of Fraction G-4 and P-4 Prior to LC-MS/MS

Fraction G-4 and P-4 from anion exchange chromatography were treated with phosphatase (E/S=1/50, w/w) in a buffer containing 10 mM Tris-HCl, 5 mM $MgSO_4$, and 1 mM $ZnCl_2$ at pH 9.0 according to the manufacturer's specification. The incubation was carried out at 37° C. for 3 h and terminated by increasing temperature to 80° C. for 10 min. Free phosphates and salts were removed by ZipTip™ pipette tip (reverse phase, 10 μL, Millipore, Billerica, Mass., USA) and peptide samples were concentrated by Savant™ Speed-Vac Concentrators (Fisher Scientific ltd., Nepean, On, Canada) for mass spectrometry analysis.

Example 10

Liquid Chromatography-Mass Spectrometry-Mass Spectrometry (LC-MS/MS)

Identification of peptides in both native and dephosphorylated G-4 fraction was carried out by a Waters ACQUITY UPLC system connected to a Waters Micro Mass Q-TOF Premier Instrument (Milford, Mass., USA). Samples were first separated by a Waters Atlantis dC18 UPLC column (150 mm×75 μm, 3 μm; Milford, Mass., USA) before MS/MS analysis. Solvent A was 0.1% formic acid in water, and solvent B was 0.1% formic acid in aceonitrile. Sample (5-10 μL) was injected to a 5 μm trapping column and trapped for 2 min at a flow rate of 10 μL/min by running 99% solvent A. The flow rate was decreased to 0.35 μL/min when the gradient was decreased from 99% A to 90% A in 5 min, to 70% A in 30 min, to 60% in 3 min, and to 5% A in 1 min. The flow rate was increased to 0.50 μL/min and held for another 2 min, and then the gradient was increased from 5% A to 98% A in 1 min and held for another 27 min. Then the flow rate was decreased to 0.35 µL/min in 1 min. The elute was ionized trough a nanoLockspray ionization source in a positive ion mode (capillary voltage of 3.80 kV and source temperature of 100° C.) before being loaded into the mass spectrometer. A Q-TOF analyzer was used to determine the mass of peptides and the mass/charge (m/z) range was set as 400-1600 in MS mode and 50-1990 in MS/MS mode. Instrument was controlled and data was collected by using MassLynx™ software (Micromass U.K. Ltd., Wythenshawe, Manchester, U.K.). Peaks Viewer™ 5.2 (Bioinformatics Solutions Inc., Waterloo, ON, Canada) was used for peptide sequencing.

Example 11

Nitrogen and Protein Determination

Crude protein and nitrogen were determined (N×6.25) in duplicate using a LECO™ FP-428 nitrogen determinator (LECO Corporation, St. Joseph, Mich., USA), and crude protein was calculated as N×6.25.

Example 12

Phosphorus Determination

The phosphorus content was determined by using a malachite green phosphate assay kit (BioAssay Systems, Hayward, Calif., USA).

Example 13

Sodium Dodecyl Sulfate Polyacrylamide Gel Electrophoresis

SDS-PAGE was conducted using a continuous system (10-20% gel) (Mini-PROTEAN Tetra Cell, Bio-Rad, Hercules, Calif., USA) (Shapiro et al., 1967). The following running buffer was used: Tris-HCl (pH 8.8) with 0.1% SDS. All samples were incubated at 95° C. for five minutes, and centrifuged at 15,000×g for five minutes. 20 µl of each supernatant was loaded onto the gel. Electrophoresis was conducted at a constant voltage of 200 V for about forty minutes. The molecular weight markers (Bio-Rad Precision Plus™ Protein Standards) included 250, 150, 100, 75, 50, 37, 25, 20, 15 and 10 kDa bands. Staining buffer was prepared as described by Hegenauer et al. (1977): 0.05% Coomassie brilliant blue R-250 in a solution of 0.1 M aluminum nitrate/25% isopropanol/10% acetic acid/1.0% Triton™ X-100. 7% acetic acid solution was used for destaining. Images of gels were captured by an Alphachem™ SP machine. Molecular weight (MW) was analyzed by AlphaEase™ FC software (version 6.0.0, Alpha Innotech Corporation, Santa Clara, Calif., USA).

Example 14

Gel Filtration HPLC

Gel filtration was carried out by HPLC (Waters, Milford, Mass., USA) in a TSK-Gel™ G3000SWXL stainless column (0.78×30 cm, Tosoh, Tokyo, JP). Phosvitin and its hydrolysate were prepared at 2 mg/mL with 0.1 M sodium phosphate buffer (containing 0.2 NaCl, pH 7.0) and filtered through a 0.45 µm PVDF filter (13 mm×0.20 µm, MANDEL, Guelph, ON, Canada) before loading to a TSK-Gel™ G3000SWxL stainless column (0.78×30 cm, Tosoh Bioscience, Inc., South San Francisco, Calif., USA). Samples (30 µL) were eluted by 0.1 M sodium phosphate buffer (containing 0.2 M NaCl, pH 7.0) at a flow rate of 0.5 mL/min on a Waters HPLC system (Waters, Milford, Mass., USA), and the elution was detected at 215 nm. System control and data analysis were performed using Empower™ II Software (Waters, Milford, Mass., USA).

REFERENCES

The following references are incorporated herein by reference (where permitted) as if reproduced in their entirety. All references are indicative of the level of skill of those skilled in the art to which this invention pertains.

Abe, Y., T. Itoh and S. Adachi (1982) Fractionation and characterization of hen's egg yolk phosvitin. *J. Food Sci.* 47:1903-1907.

Adamson, N. J. and Reynolds, E. C. (1995) Characterization of tryptic casein phosphopeptides prepared under industrially relevant conditions. *Biotechnology and Bioengineering* 45(3), 196-204.

Adamson, N. J. and Reynolds, E. C. (1997) Relationship between degree of casein hydrolysis and phosphopeptide release. *J Dairy Res.* 64(4), 505-514.

Albright, K. J., D. T. Gordon and O. J. Cotterill (1984) Release of iron from phosvitin by heat and food additives. *J. Food Sci.* 49:78-81.

Alderton, G. and Fevold, H. L. (1945) Preparation of the egg yolk lipoprotein, lipovitellin. *Archives of Biochemistry* 8(3), 415-419.

Anton, M., O. Castellani and C. Guerin-Dubiard (1998) Bioactive Egg Compounds. Huopalahti, R., R. Lopez-Fandino, M. Anton, and R. Schade. eds. Springer, Verlag Berlin Heidelberg, German, pp. 17-24.

Anton, M., M. Le Denmat and G. Gandemer (2000) Thermostability of hen egg yolk granules: contribution of native structure of granules. *J Food Sci.* 65:581-584.

Bennich, H., Johansson, B. and Osterberg, R. (1959) A phosphopeptide isolated from bovine alpha-casein after tryptic hydrolysis. *Acta chemica Scandinavica* 13(6), 1171-1175.

Byrne, B. M., A. D. van het Ship, J. A. M. van der Klundert, A. C. Arnberg and M. Gruber (1984) Amino acid sequence of phosvitin derived from the nucleotide sequence of part of the chicken vetellogenin gene. Biochem. 23:4275-4279.

Burley, R. W. and Vadehra, D. V. (1989) The Avian Egg Chemistry and Biology. Wiley-Interscience.

Burley, R. W. and W. H. Cook (1961) Isolation and composition of avian egg yolk granules and their constituents α- and β-lipovitellins. *Can J Biochem Physiol.* 39:1295-1307.

Byrne, B. M., Schip, A. D. V., Vandeklundert, J. A. M., Arnberg, A. C., Gruber, M. and Ab, G. (1984) Amino-acid-sequence of phosvitin derived from the nucleotide-sequence of part of the chicken vitellogenin gene. *Biochemistry* 23(19), 4275-4279.

Castellani, O., V. Martinet, E. David-Briand, C. Guerin-Dubiard, and M. Anton (2003) Egg yolk phosvitin: preparation of metal-free purified protein by fast protein liquid chromatography using aqueous solvents. *J Chromatogr B.* 791:273-284.

Causeret, D., E. Matringe, and D. Lorient (1991) Ionic strength and pH effects on composition and microstructure of yolk granules. *J. Food Sci.* 56:1532-1536.

Causeret, D., E. Matringe, and D. Lorient (1991) Mineral cations affect microstructure of egg yolk granules. *J. Food Sci.* 57:1323-1326.

Chang, C. M., Powrie, W. D. and Fennema, O. (1977) Microstructure of egg-yolk. *J. Food Sci.* 42(5), 1193-1200.

Chay Pak Ting, B. P., Mine, Y., Juneja, L. R., Okubo, T., Gauthier, S. F. and Pouliot, Y. (2011) Comparative composition and antioxidant activity of peptide fractions obtained by ultrafiltration of egg yolk protein enzymatic hydrolysates. *Membranes* 1(3), 149-161.

Choi, I., C. Jung, H. Choi, C. Kim and H. Ha (2005) Effectiveness of phosvitin peptides on enhancing bioavailability of calcium and its accumulation in bones. *Food Chem.* 93(4):577-583.

Chung, S. L., and L. K. Ferrier (1992) pH and sodium chloride effects on emulsifying properties of egg yolk phosvitin. *J. Food Sci.* 57:40-42.

Clark, R. C. (1970) The isolation and composition of two phosphoproteins from hen's egg. *Biochem. J.* 118:537-542.

Clark, R. C. (1985) The primary structure of avian phosvitins-contributions through the Edman degradation of methylmercaptovitins prepared from the constituent phosphoproteins. *Int. J. Biochem.* 17(9), 983-988.

Cross, K. J., Huq, N. L., Palamara, J. E., Perich, J. W. and Reynolds, E. C. (2005) Physicochemical characterization of casein phosphopeptide-amorphous calcium phosphate nanocomplexes. *J. Biol. Chem.* 280(15), 15362-15369.

Ellegard, K. H., Gammelgard-Larsen, C., Sørensen, E. S, and Fedosov, S. (1999) Process scale chromatographic isolation, characterization and identification of tryptic bioactive casein phosphopeptides. *Int. Dairy J.* 9(9), 639-652.

Feng, F. Q. and Mine, Y. (2006) Phosvitin phosphopeptides increase iron uptake in a Caco-2 cell monolayer model. *Int. J. Food Sci. and Technol.* 41(4), 455-458.

Finn, R. N. (2007) Vertebrate yolk complexes and the functional implications of phosvitins and other subdomains in vitellogenins. *Biology of Reproduction* 76(6), 926-935.

Goulas, A., Triplett, E. L. and Taborsky, G. (1996) Oligophosphopeptides of varied structural complexity derived from the egg phosphoprotein, phosvitin. *J. Protein Chem.* 15(1), 1-9.

Greengard, O., Mendelsohn, N. and Sentenac, A. (1964) Phosvitin iron carrier of egg yolk. *Biochimica et Biophysica Acta* 90(2), 406-407.

Grogan, J., Shirazi, A. and Taborsky, G. (1990) Phosphorus nuclear-magnetic-resonance of diverse phosvitin species. *Comparative Biochemistry and Physiology Part B: Biochemistry & Molecular Biology* 96(4), 655-663.

Hartmann, R. and Meisel, H. (2007) Food-derived peptides with biological activity: from research to food applications. *Current Opinion in Biotechnology* 18(2), 163-169.

Hata, I., Higashiyama, S, and Otani, H. (1998) Identification of a phosphopeptide in bovine alpha(s1)-casein digest as a factor influencing proliferation and immunoglobulin production in lymphocyte cultures. *J. Dairy Res.* 65(4), 569-578.

Hegenauer, J., L. Ripley and G. Nace (1977) Staining acidic phosphoproteins in electrophoretic gels. *Anal Biochem.* 78:308-311.

Ishikawa, S. I., Tamaki, S., Arihara, K. and Itoh, M. (2007) Egg yolk protein and egg yolk phosvitin inhibit calcium, magnesium, and iron absorptions in rats. *J. Food Sci.* 72(6), S412-S419

Jiang, B. and Mine, Y. (2000) Preparation of novel functional oligophosphopeptides from hen egg yolk phosvitin. *Journal of Agricultural and Food Chemistry*, 48(4), 990-994.

Kahn, M. A., Babiker, E. E., Azakami, H. and Kato, A. (1999) Molecular mechanism of the excellent emulsifying properties of phosvitin-galactomannan conjugate. *Journal of Agricultural and Food Chemistry* 47(6), 2262-6.

Katayama, S., Xu, X. M., Fan, M. Z. and Mine, Y. (2006). Antioxidative stress activity of oligophosphopeptides derived from hen egg yolk phosvitin in Caco-2 cells. *Journal of Agricultural and Food Chemistry* 54(3), 773-778.

Katayama, S., Ishikawa, S., Fan, M. Z. and Mine, Y. (2007) Oligophosphopeptides derived from egg yolk phosvitin up-regulate gamma-glutamylcysteine synthetase and antioxidant enzymes against oxidative stress in caco-2 cells. *Journal of Agricultural and Food Chemistry*, 55(8), 2829-2835.

Katayama, S., Fan, M. Z., Ishikawa, S, and Mine, Y. (2006). Phosphopeptides derived from egg yolk phosvitin up-regulate gamma-glutamylcysteine synthetase and antioxidant enzymes against oxidative stress in human intestinal epithelial cells. *Abstracts of Papers of the American Chemical Society* 232, 345-345.

Kawahara, T. and Otani, H. (2004). Stimulatory effects of casein phosphopeptide (CPP-III) on mRNA expression of cytokines in Caco-2 cells. *Bioscience Biotechnology and Biochemistry* 68(8), 1779-1781.

Kitts, D. D. and Nakamura, S. (2006) Calcium-enriched casein phosphopeptide stimulates release of IL-6 cytokine in human epithelial intestinal cell line. *J. Dairy Res.* 73(1), 44-48.

Kitts, D. D. (1994) Bioactive substances in food-identification and potential uses. *Canadian I Physiology and Pharmacology* 72(4), 423-434.

Khan, M. S., Babiker, E. E., Azakami, H., & Kato, A. (1998). Effect of protease digestion and dephosphorylation on high emulsifying properties of hen egg yolk phosvitin. *Journal of Agricultural and Food Chemistry*, 46(12), 4977-4981.

Korhonen, H. and Pihlanto, A. (2006) Bioactive peptides: production and functionality. *International Dairy Journal* 16(9), 945-960.

Kurisaki, J., Yamauchi, K., Isshiki, H. and Ogiwara, S. (1981) Differences between alpha-lipovitellin and beta-lipovitellin from hen egg-yolk. *Agr. Biol. Chem.* 45(3), 699-704.

Losso, J. N., and S, Naki (1994) A Simple Procedure for the Isolation of Phosvitin from Chicken Egg Yolk. J. S. Sim and S. Nakai. ed. CAB INTERNATIONAL, Wallingford, Oxon, UK., pp. 151-157.

McBee, L. E., and O. J. Cotterill (1979) Ion-exchange chromatography and electrophoresis of egg yolk proteins. *J. Food Sci.* 44:656-667.

Mecham, D. K., and H. S. Olcott (1949) Phosvitin, the principal phosphoprotein of egg yolk. *J. Amer. Chem. Soc.* 71:3670-3679.

Meisel, H., Bernard, H., Fairweather-Tait, S., FitzGerald, R. J., Hartmann, R., Lane, C. N., McDonagh, D., Teucher, B. and Wal, J. M. (2003). Detection of caseinophosphopeptides in the distal ileostomy fluid of human subjects. *British Journal of Nutrition* 89(3), 351-358.

Mellander, O. (1950). The physiological importance of the casein phosphopeptide calcium salts. II. Peroral calcium dosage of infants. Some aspects of the patho-genesis of rickets. *Acta Soc Med Upsaliensis* 55((5/6)), 247-255.

Mellander, O. and Isaksson, B. (1950). The physiological importance of the casein phosphopeptide calcium salts. I. Intravenous and peroral calcium dosage in animal experiments. *Acta Soc Med Upsaliensis* 55((5/6)), 239-246.

Morris, E. R. and Greene, F. E. (1972) Utilization of Iron of Egg-Yolk for Hemoglobin Formation by Growing Rat. *Journal of Nutrition*, 102(7), 901-908.

Nakamura, S., M. Ogawa, S, Nakai, A. Kato, and D. D. Kitts (1998) Antioxidant activity of a maillard-type phosvitin-galactomannan conjugate with emulsifying properties and heat stability. *J. Agric. Food. Technol.* 46:3958-3963.

Otani, H. and Wakatsuki, S. (2004) Reduction of allergic symptoms in NC/Jic Jcl mice fed a diet containing casein phosphopeptide preparation, CPP-III. *Animal Science Journal* 75(2), 147-153.

Peterson, R. F., Nauman, L. W. and Mcmeekin, T. L. (1958) The separation and amino acid composition of a pure phosphopeptone prepared from beta-Casein by the action of trypsin. *J. Amer. Chem. Soc.* 80(1), 95-99.

Powrie, W. D., and S, Nakai (1986) The chemistry of eggs and egg products. In Egg science and technology, 3$^{rd}$ ed. Westport, Conn.: AVI Publishing Co., pp. 97-139.

Reynolds, E. C., Black, C. L., Cai, F., Cross, K. J., Eakins, D., Huq, N. L., Morgan, M. V., Nowicki, A., Perich, J. W., Riley, P. F., Shen, P., Talbo, G. and Webber, F. (1999) Advances in enamel remineralization: casein phosphopeptide-amorphous calcium phosphate. *J. Clin. Dent.* 10(2), 86-88.

Sattar Khan, M. A., S, Nakamura, M. Ogawa, E. Akita, H. Azakami and E. Kato (2000) Bactericidal action of egg yolk phosvitin against *Escherichia coli* under thermal stress. *J. Agric. Food. Chem.* 48:1503-1506.

Schlimme, E. and Meisel, H. (1995) Bioactive peptides derived from milk-proteins—structural, physiological and analytical aspects. *Nahrung-Food* 39(1), 1-20.

Shapiro, A. L., Vinuela, E. and Maizel, J. V. (1967) Molecular weight estimation of polypeptide chains by electrophoresis in SDS-polyacrylamide gels. *Biochem. Biophys. Res. Comm.* 28(5), 815-820.

Sundararajan, T. A., K. S. V. Sampath Kumar and P. S. Sarma (1960) A simplified procedure for the preparation of phosvitin and vitellin. *Biochim. Biophys. Acta.* 38:360-362.

Swaisgood, H. E. (1992) Chemistry of the caseins. *Adv. Dairy Chem.* 2, 63-110.

Swaisgood, H. E. (2003) Chemistry of the caseins. *Adv. Dairy Chem.* 1, 139-187.

Taborsky, G. (1983) Phosvitin. *Advances in Inorganic Biochemistry* 5, 235-279.

Ternes, W. (1989) Characterization of water soluble egg yolk proteins with isoelectric focusing. *J. Food Sci.* 54:764-765.

Tsutsui, T., and T. Obara (1984) Preparation and characterization of phosvitin from hen's egg yolk granule. *Agric. Biol. Chem.* 48:1153-1160.

Wallace, R. A., and J. P. Morgan (1986) Chromatographic resolution of chicken phosvitin. *Biochem. J.* 240:871-878.

Wallace, R. A., and J. P. Morgan (1986) Isolation of phosvitin: retention of small molecular weight species and characteristics on electrophoretic gels. *Anal Bioch.* 157:256-261.

West, D. W. and Towers, G. E. (1976) Study of enzymic dephosphorylation of beta-casein and a derived phosphopeptide. *Biochimica et biophysica acta* 453(2), 383-390.

Xu, X., Katayama, S, and Mine, Y. (2007) Antioxidant activity of tryptic digests of hen egg yolk phosvitin. *J. Sci. Food Agric.* 87(14), 2604-2608.

Young, D., Nau, F., Pasco, M. and Mine, Y. (2011) Identification of hen egg yolk-derived phosvitin phosphopeptides and their effects on gene expression profiling against oxidative stress-induced Caco-2 cells. *J. Agric. Food Chem.* 59(17), 9207-9218.

Young, D., Fan, M. Z. and Mine, Y. (2010) Egg yolk peptides up-regulate glutathione synthesis and antioxidant enzyme activities in a porcine model of intestinal oxidative stress. *J. Agric. Food Chem.* 58(13), 7624-7633.

Zhao, L., Wang, Z. and Xu, S. Y. (2007) Preparation of casein phosphorylated peptides and casein non-phosphorylated peptides using alcalase. *European Food Res. Technol.* 225 (3-4), 579-584.

---

What is claimed is:

1. A process for extracting phosvitin from egg yolk comprising the steps of:
   a) contacting the egg yolk or egg yolk protein granules with a salt solution to form a mixture comprising phosvitin and non-phosvitin proteins in solution;
   b) adjusting the pH of the mixture to 7.0 or below and above about 3.5 to precipitate non-phosvitin proteins and leave phosvitin substantially in solution;
   c) separating precipitated proteins; and
   d) recovering a solution or supernatant comprising phosvitin.

2. The process of claim 1, wherein the egg yolk is diluted and mixed with water to produce egg yolk protein granules.

3. The process of claim 1, wherein pH of the mixture is about 7.

4. The process of claim 1, wherein the egg yolk or egg yolk protein granules are mixed with the salt solution at a temperature of about 4° C.

5. The process of claim 1, wherein the egg yolk is mixed with the salt solution and heated.

6. The process of claim 5 wherein the mixture is heated to about 80° C.

7. The process of claim 1, wherein the salt solution is a 10% sodium chloride solution.

8. The process of claim 1, wherein the pH is adjusted to a pH of about 5.0 or lower.

9. The process of claim 1, wherein in step (c) the mixture is centrifuged to remove precipitated components.

10. A process of preparing phosvitin phosphopeptides, comprising the steps of extracting phosvitin from egg yolk using the method of claim 1, dephosphorylating the phosvitin and hydrolyzing the dephosphorylated phosvitin.

11. The process of claim 10 wherein the phosvitin is dephosphorylated with an alkaline solution.

12. The process of claim 11 wherein the alkaline solution comprises NaOH.

13. The process of claim 10, wherein the phosvitin is hydrolyzed with a protease.

14. The process of claim 13 wherein the protease comprises pancreatin.

15. The process of claim 14, wherein hydrolysis is conducted using pancreatin at an enzyme/substrate ratio of about 1:50 (w/w).

16. The process of claim 14 wherein the phosvitin is hydrolyzed to a degree of hydrolysis of greater than about 6%, or greater than about 10%.

17. The process of claim 16 wherein the degree of hydrolysis is about 12.9%.

18. The process of claim 14 wherein the hydrolysate has a nitrogen to phosphorus (N/P) of less than about 5, or less than about 4.

19. The process of claim 10, which does not use an organic solvent or a non-food compatible chemical.

20. Phosvitin extract obtained by the process of claim 1, having a purity in a range of about 50% to about 95%.

21. The phosvitin extract of claim 20 having a purity of greater than about 75%, or greater than about 80%.

22. A phosphopeptide derived from the phosvitin extract of claim 20.

23. A pharmaceutical or nutraceutical composition, or a cosmetic or dental product, or a foodstuff, comprising a phosphopeptide of claim 22, or both.

24. A method of promoting health by administering to a subject the phosphopeptide of claim 22, in an amount sufficient to effect a health benefit.

* * * * *